(12) United States Patent
Piazza et al.

(10) Patent No.: US 11,186,534 B2
(45) Date of Patent: Nov. 30, 2021

(54) DERIVATIVES OF SULINDAC CAN PROTECT NORMAL CELLS AGAINST OXIDATIVE DAMAGE

(71) Applicant: University of South Alabama, Mobile, AL (US)

(72) Inventors: Gary Piazza, Daphne, AL (US); Xi Chen, Hoover, AL (US); Herbert Weissbach, Boynton Beach, FL (US); Shailaja Kesraju Allani, Boynton Beach, FL (US)

(73) Assignee: UNIVERSITY OF SOUTH ALABAMA, Mobile, AL (US)

( * ) Notice: Subject to any disclaimer, the term of this patent is extended or adjusted under 35 U.S.C. 154(b) by 0 days.

(21) Appl. No.: 16/495,013

(22) PCT Filed: Mar. 16, 2018

(86) PCT No.: PCT/US2018/022885
§ 371 (c)(1),
(2) Date: Sep. 17, 2019

(87) PCT Pub. No.: WO2018/170410
PCT Pub. Date: Sep. 20, 2018

(65) Prior Publication Data
US 2020/0095184 A1    Mar. 26, 2020

Related U.S. Application Data

(60) Provisional application No. 62/472,785, filed on Mar. 17, 2017.

(51) Int. Cl.
*C07C 59/72* (2006.01)
*A61P 9/10* (2006.01)

(52) U.S. Cl.
CPC ............... *C07C 59/72* (2013.01); *A61P 9/10* (2018.01)

(58) Field of Classification Search
CPC ..................................................... C07C 59/72
See application file for complete search history.

(56) References Cited

U.S. PATENT DOCUMENTS

| | | | |
|---|---|---|---|
| 5,965,619 A | 10/1999 | Pamukcu et al. | |
| 6,121,321 A | 9/2000 | Sperl et al. | |
| 8,044,048 B2* | 10/2011 | Piazza | C07C 323/62 |
| | | | 514/238.8 |
| 9,365,528 B2* | 6/2016 | Reynolds | A61P 1/04 |
| 9,862,698 B2* | 1/2018 | Piazza | A61K 45/06 |
| 9,931,315 B2* | 4/2018 | Piazza | A61P 35/00 |
| 10,526,307 B2* | 1/2020 | Piazza | A61K 31/341 |
| 2006/0235080 A1* | 10/2006 | Weissbach | A61K 31/4439 |
| | | | 514/569 |
| 2012/0295979 A1 | 11/2012 | Prentice et al. | |
| 2016/0168113 A1 | 6/2016 | Piazza et al. | |

FOREIGN PATENT DOCUMENTS

WO    WO 2016100542 A    *    6/2016

OTHER PUBLICATIONS

Moench et al. PNAS 2009, 106, 19611-1916 (Year: 2009).*
International Search Report for PCT/US2018/022885, dated Aug. 8, 2018.

* cited by examiner

*Primary Examiner* — Matthew P Coughlin
(74) *Attorney, Agent, or Firm* — Burns & Levinson, LLP; Shawn P. Foley

(57) ABSTRACT

The disclosure provides chemical compounds possessing therapeutic and/or protective properties against oxidative damage. Methods of making such therapeutic and/or protective compounds and associated compositions are also provided, as are methods for their use, which include protecting cells from oxidative damage and/or inhibiting production of ROS in a cell or subject, as well as preventing or reducing the extent of tissue damage caused by an ischemic event in a subject at elevated risk of such an event.

28 Claims, 9 Drawing Sheets

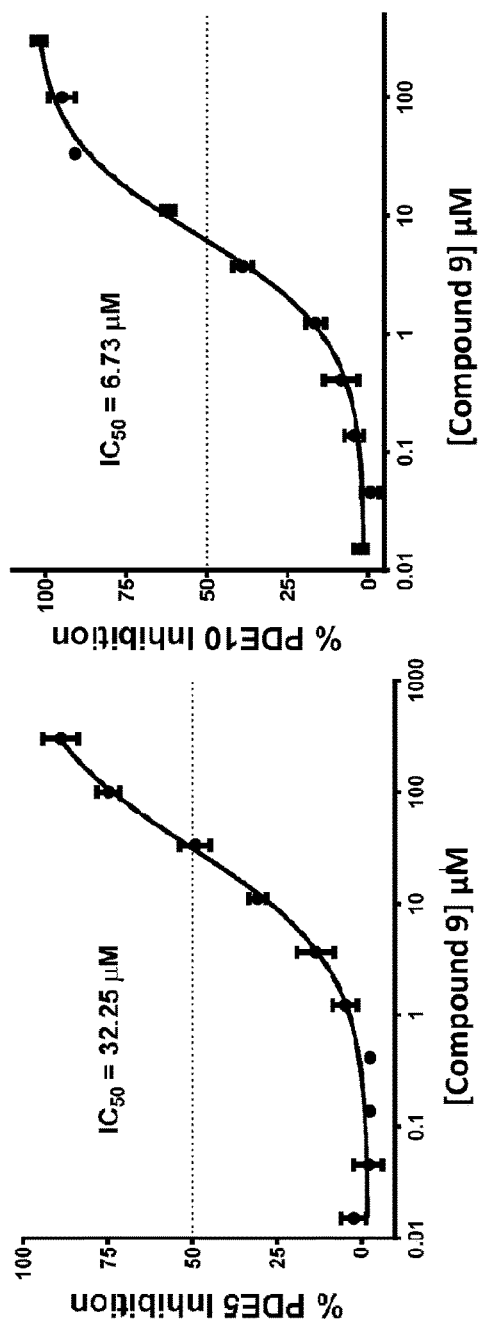
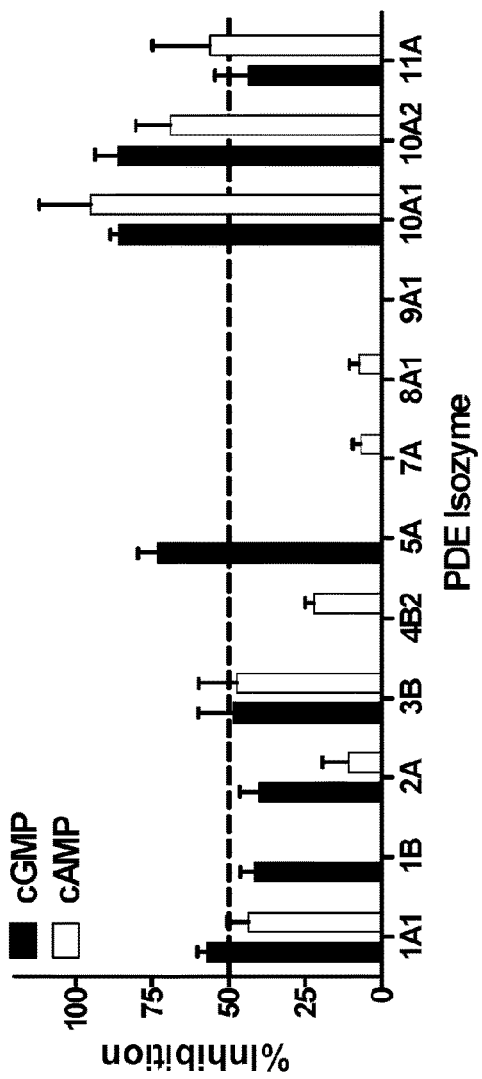
FIGURE 5A
FIGURE 5B
FIGURE 5C

DERIVATIVES OF SULINDAC CAN PROTECT NORMAL CELLS AGAINST OXIDATIVE DAMAGE

CROSS-REFERENCE TO RELATED APPLICATIONS

This application is a U.S. National Phase entry under 35 U.S.C. § 371 of International Application No. PCT/US2018/022885, filed Mar. 16, 2017, published in English, which claims the benefit of priority under 35 U.S.C. § 119(e) to U.S. Provisional Application No. 62/472,785, filed on Mar. 17, 2017, entitled, "Derivatives of Sulindac Can Protect Normal Cells Against Oxidative Damage". The contents of these related applications are incorporated herein by reference in their entireties.

GOVERNMENTAL SUPPORT

Development of the present invention was supported, at least in part, by the National Cancer Institute of the National Institutes of Health under Award Number 1R01CA131378. Therefore, the Government may have certain rights in the invention.

BACKGROUND OF THE INVENTION

Oxygen is involved in a wide range of normal metabolic reactions and is essential for the survival of all aerobic organisms, including human beings. Reactive oxygen species (ROS), such as superoxide, are produced in abundance as a byproduct of the incomplete reduction of oxygen that has entered the respiratory chain. Superoxide is the precursor of other damaging oxygen species includes hydrogen peroxide, the hypochlorite ion and the hydroxyl radical. Oxidase enzymes in cells such as phagocytes and nitric oxide synthases are other sources of ROS.

While low levels of ROS are present under normal physiological conditions, in excess, ROS can cause oxidative damage to cells and tissues by, for example, oxidizing cellular macromolecules such as nucleic acids, lipids and proteins. Cumulative damage to cells in this manner can result in pathology. Not surprisingly, oxidative damage has been implicated in a wide variety of diseases and conditions including chronic obstructive lung disorders such as smoker's emphysema, reperfusion disease, neurodegenerative diseases such as Alzheimer's disease, Parkinson's disease, and amyotrophic lateral sclerosis (ALS), heart attacks, stroke, several autoimmune diseases and cancer.

The balance between the cellular production of reactive oxygen species (ROS), primarily from mitochondrial respiration, and the ability of cells to protect against oxidative damage very likely also determines the rate and extent of the normal aging process in humans and other mammals. Our laboratory initially became interested in the role of cellular protective mechanisms against oxidative damage after identifying methionine sulfoxide reductase A (MsrA), the first member of the Msr family of enzymes (1). MsrA reduces methionine sulfoxide residues (S epimer) in proteins back to methionine, repairing oxidative damage. The other major Msr family member is MsrB, which reduces the R epimer of methionine sulfoxide in proteins (2). The Msr system is also part of a ROS scavenger system that permits methionine residues in proteins to function as catalytic anti-oxidants (3). Overexpression of mammalian MsrA in *D. melanogaster* was reported to extend their lifespan (4), while MsrA has been shown to be involved in the extension of the lifespan of *C. elegans* mutants lacking the daf 2 gene (5) and on calorie restricted diets (6).

Small molecules that contain a methyl sulfoxide moiety, such as the anti-inflammatory drug sulindac, can also serve as substrates for the Msr enzymes. It is known that MsrA can reduce the S epimer of sulindac. Recently, we have described a protein purified from liver extracts that can reduce the R epimer of sulindac (7). As shown in FIG. 1, sulindac is a mixture of both epimers and a pro drug containing a methyl sulfoxide group that can be converted by these enzymes to sulindac sulfide, the active metabolite of sulindac responsible for its cyclooxygenase COX inhibitory activity (7). Initial studies with sulindac also showed unexpected properties of this drug. For example, sulindac at concentrations that were not cytotoxic, could sensitize cancer cells to oxidizing agents, resulting in enhanced anticancer activity (8). However, under similar conditions sulindac protected normal lung cells against oxidative damage by a mechanism that was independent of its COX inhibitory activity or the Msr system (8). As shown in further studies of ischemia/reperfusion damage to the heart (9) and oxidative and UV damage to retinal pigmented epithelial (RPE) cells (10), sulindac is able to initiate a protective pharmacological preconditioning response by a mechanism similar to the well documented protective mechanism, referred to as ischemic preconditioning (IPC)(11). However, unlike IPC which is initiated by sub-lethal hypoxic conditions, the protective effect of sulindac was obtained under normoxic conditions, which we refer to as pharmacological preconditioning.

Long term uses of nonsteroidal anti-inflammatory drugs (NSAIDS) such as sulindac are limited by gastrointestinal, renal and cardiovascular toxicities, which are caused by the inhibition of COX-1 and COX-2 and suppression of physiologically important prostaglandins. Sulindac sulfone, a metabolic oxidation product of sulindac, has no COX inhibitory activity, but is more active than sulindac in protecting cells against oxidative damage, which suggests that the cytoprotective mechanism is not related to the COX inhibitory activity of sulindac (8, 10). However, sulindac sulfone is significantly more toxic to cells relative to sulindac.

Thus, it would be advantageous to make sulindac derivatives that are non-cytotoxic, but more potent in protecting cells against oxidative damage and that lack COX inhibitory activity.

SUMMARY OF THE INVENTION

A first aspect of the present invention is directed to chemical compounds, represented by formulas (I) and (II), herein, or pharmaceutically acceptable salts thereof. A second aspect of the present invention is directed to methods of making the chemical compounds. A third aspect of the present invention is directed to pharmaceutical compositions containing an effective amount of a compound of formula (I) or (II), and optionally a pharmaceutically acceptable carrier. A fourth aspect of the present invention is directed to a method of treating a subject with a disease or condition the cause or progression of which involves the production of reactive oxygen species (ROS) and resultant oxidative stress, which entails administering to the subject a therapeutically effective amount of a compound of formula (I) or (II). A related aspect is directed to a method for protecting cells in a subject from oxidative damage, e.g., caused by a reperfusion injury, which entails administering to the subject an effective amount of a compound of formula (I) or (II). A further aspect is directed to a method of inhibiting production of ROS in a cell, in vivo or in vitro, that involves contacting the cell with an effective amount of a compound of formula (I) or (II). A further aspect is directed to a method of protecting normal cells against oxidative damage, in vivo or in vitro, e.g., by environmental factors such as UV irradiation or diseases, that involves contacting the cell with effective amount of a compound of formula (I) or (II).

An additional aspect of the present invention provides a method of preventing or reducing the extent of tissue damage of an ischemic event in a subject at elevated risk of an ischemic event, the method involving identifying a subject at elevated risk of an ischemic event and administering a therapeutically effective amount of the compound (Z)-2-(5,6-dimethoxy-2-methyl-1-(3,4,5-trimethoxybenzylidene)-1H-inden-3-yl)acetic acid, or a pharmaceutically acceptable salt or prodrug thereof to the subject, thereby preventing or reducing the extent of tissue damage of an ischemic event in the subject identified as being at elevated risk of an ischemic event.

In one embodiment, the subject possesses one or more of the following risk factors for an ischemic event: high blood pressure, heart disease, high cholesterol levels, sleep apnea, previous occurrence of stroke, smoking, excessive alcohol consumption and excessive weight. Optionally, the ischemic event is an ischemic event of a tissue selected from the group consisting of the heart, brain, kidneys and liver.

In certain embodiments, the method further involves administering to the subject a therapeutically effective amount of aspirin, a blood pressure medication, a type II diabetes medication and/or an mTOR inhibitor. In one embodiment, the type II diabetes medication is metformin. In certain embodiments, (Z)-2-(5,6-dimethoxy-2-methyl-1-(3,4,5-trimethoxybenzylidene)-1H-inden-3-yl)acetic acid, or a pharmaceutically acceptable salt or prodrug thereof and the aspirin, blood pressure medication, type II diabetes medication and/or mTOR inhibitor are co-administered to the subject Compounds of the present invention, e.g., Compound 9 as described herein, are significantly more potent than sulindac in protecting cells from oxidative damage, and exhibit essentially no COX inhibitory activity. Without intending to be bound to any particular theory of operation, the mechanism of action of the inventive compounds may be related to their ability to inhibit cyclic nucleotide degrading phosphodiesterase (PDE) isozymes such as PDE5 and/or PDE10, resulting in an increase in intracellular cGMP and/or cAMP levels that could initiate a pharmacological preconditioning response.

BRIEF DESCRIPTION OF THE DRAWINGS

FIG. 4 shows that Compound 9 lacks significant COX inhibitory activity.

FIG. 5 shows PDE inhibitory activity of Compound 9. FIG. 5A shows concentration-dependent inhibition of PDE5 by Compound 9. FIG. 5B shows concentration-dependent inhibition of PDE10 by Compound 9. FIG. 5C shows the ability of Compound 9 to inhibit other PDE isozymes when tested against a panel of PDE isozymes at a 25 µM concentration.

FIG. 8A shows results obtained for hearts obtained from rats initially administered no drug or Compound 9, exposed to ischemia and reperfusion, stained with 1% TTC, then cut transversely into 2-mm sections. Percent infarction was determined using NIH image J analysis software. Histograms represent percent of heart that was infarcted. (n=one animal administered Compound 9, as compared to four animals administered no compund). FIG. 8B shows photographs of representative sections from Langendorff hearts subjected to TTC staining following 45 min ischemia and 2 h reperfusion, showing infarcted tissue (white) and viable tissue (red).

DETAILED DESCRIPTION

I. Definitions

Figure 1:
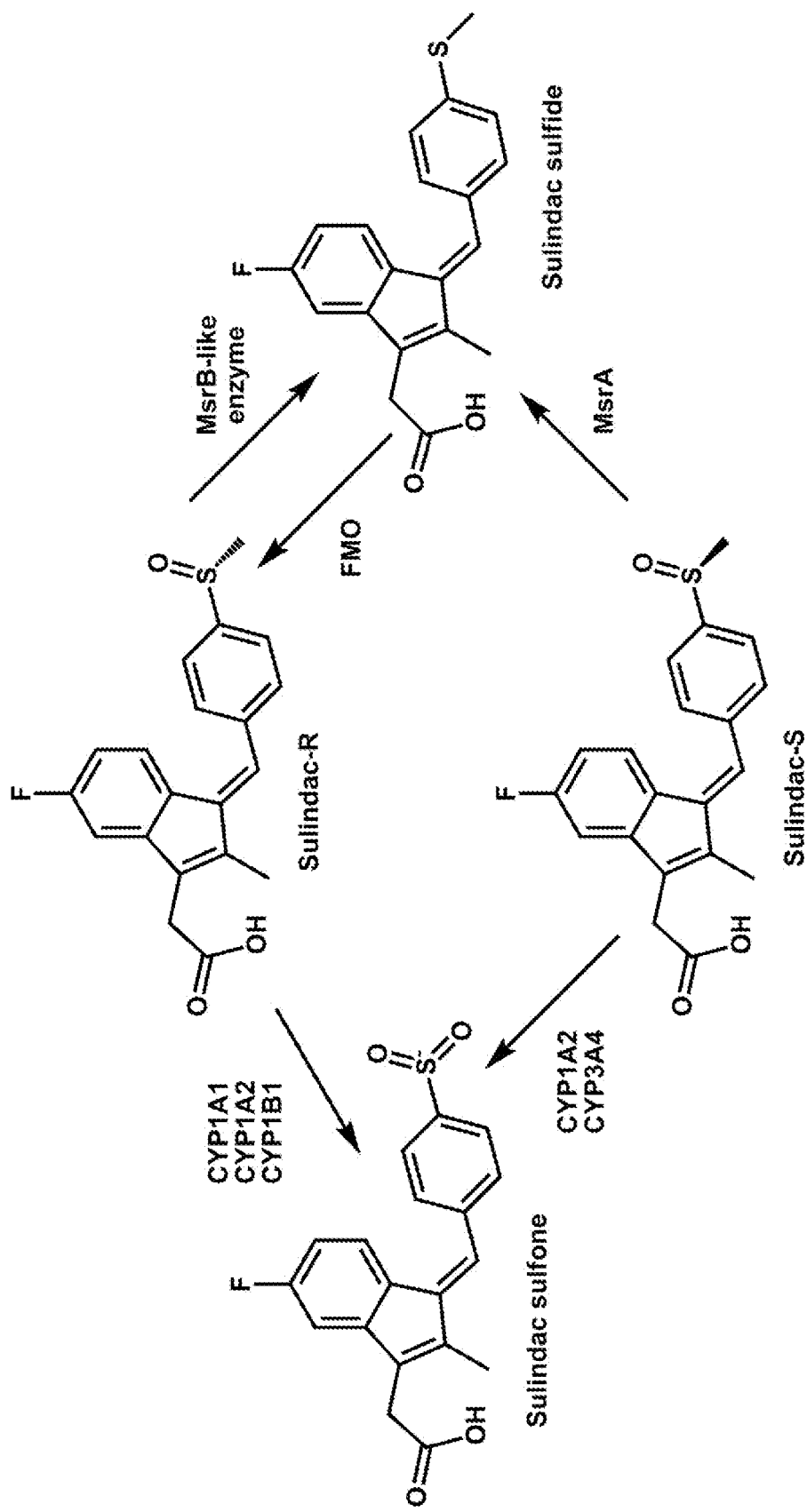
FIG. 1 shows the structure of sulindac and its metabolites. MsrA and MsrB1 can reduce the S and R epimers of sulindac, respectively, to sulindac sulfide, the active COX inhibitor. The oxidation of the epimers is catalyzed by members of the cytochrome (CYP)-P-450 system.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atoms in the structures herein indicates the presence of a hydrogen, unless indicated otherwise.

When indicating the numbers of substituents, the term "one or more" refers to the range from one substituent to the highest possible number of substitution, i.e., replacement of one hydrogen up to replacement of all hydrogens by substituents.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e., replacement of one hydrogen up to replacement of all hydrogens by substituents.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "halo", "halogen", and "halide" are used interchangeably herein and denote fluorine, chlorine, bromine and iodine.

The term "alkyl" denotes a monovalent linear or branched saturated hydrocarbon group of 1 to 12 carbon atoms. In particular embodiments, alkyl has 1 to 7 carbon atoms, and in some embodiments 1 to 4 carbon atoms, and in yet other embodiments, 1, 2 or 3 carbon atoms. Examples of alkyl include methyl, ethyl, propyl, isopropyl, n-butyl, iso-butyl, sec-butyl, or tert-butyl, and particularly methyl.

The term "alkenyl denotes a monovalent linear or branched hydrocarbon group of 2 to 7 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl, and iso-butenyl.

The term "alkynyl" denotes a monovalent linear or branched saturated hydrocarbon group of 2 to 7 carbon atoms comprising one, two or three triple bonds. In particular embodiment's alkynyl has from 2 to 4 carbon atoms comprising one or two triple bonds. Examples of alkynyl include ethynyl, propynl, prop-2-ynyl, isopropynyl, and n-butynyl.

The term "alkoxy" denotes a group of the formula —O—R', wherein R' is an alkyl group. Examples of alkoxy moieties include methoxy, ethoxy, isopropoxy, and tert-butoxy, and particularly methoxy.

The term "carbocyclic" denotes a monovalent saturated or aromatic monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloakyl are bicyclo[2.2.1]heptanyl, or bicyclo[2.2.2]octanyl.

The term "heterocyclic" denotes a monovalent saturated or partly unsaturated aromatic monocyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, and oxazepanyl.

The term "aromatic" denotes the conventional idea of aromaticity as defined in the literature, in particular in *IUPAC—Compendium of Chemical Terminology,* 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl.

The term "aryl(alkyl)oxy" denotes a group of the formula —O—$(CH_2)_n$—R' wherein R' is aryl (e.g., phenyl), and n is 0, 1 or 2. An example of arylalkyloxy is benzyloxy.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl, most particularly pyrazolyl and pyridinyl.

The term "alkylene" denotes a linear saturated divalent hydrocarbon group of 1 to 7, e.g., 1-2 or 1-3 carbons, carbon atoms or a divalent branched saturated divalent hydrocarbon group of 3 to 7 carbon atoms. Examples of alkylene groups include methylene, ethylene, propylene, 2-methylpropylene, butylene, 2-ethylbutylene, pentylene and hexylene.

The term "alkylamino" denotes a group —NR'R", wherein R' is hydrogen and R" is an alkyl, e.g., C1-3 alkyl such methyl. The term "dialkylamino" as used herein denotes a group —NR'R", wherein R' and R" are both alkyl. Examples of alkylamino groups include methylamino and ethylamino. Examples of alkylamino groups include dimethylamino, methylethylamino, diethyl amino and di(1-methylethyl)amino.

The terms "pharmaceutical composition" and "pharmaceutical formulation" (or "formulation") are used interchangeably and denote a mixture or solution comprising a therapeutically effective amount of an active pharmaceutical ingredient together with one or more pharmaceutically acceptable carriers to be administered to a subject, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

When the compounds of this invention are solids, it is understood by those skilled in the art that the compounds described herein, and their solvates and salts, may exist in different solid forms, particularly different crystal forms, all of which are intended to be within the scope of the present invention and specified formulas.

The term "pharmaceutically acceptable salts" denotes salts which are not biologically or otherwise undesirable. Pharmaceutically acceptable salts include acid addition salts. The terms "pharmaceutically acceptable excipient" and "pharmaceutically acceptable carrier" denote any pharmaceutically acceptable ingredient in a pharmaceutical composition that is physiologically acceptable and, has no therapeutic activity, and is non-toxic to the subject administered and inert with respect to the compound of formulas (I) and (II), and any other active agent that may be present in the composition.

A "subject" is a mammal. Mammals include domesticated animals (e.g., cows, sheep, cats, dogs, and equines such as horses), primates (e.g., humans and non-human primates such as monkeys), rabbits, and rodents (e.g., mice and rats). In certain embodiments, the subject is a human.

As used herein "amelioration" or "treatment" (or "treating") is understood as meaning to lessen or decrease at least one sign, symptom, indication, or effect of a specific disease or condition. For example, amelioration or treatment of retinitis pigmentosa (RP) can be to reduce, delay, or eliminate one or more signs or symptoms of RP such as a reduction in night vision, a reduction in overall visual acuity, a reduction in visual field, a reduction in the cone density in one or more quadrants of the retina, thinning of retina, particularly the outer nuclear layer, reduction in a- or b-wave amplitudes on scotopic or photopic electroretinograms (ERGs); or any other clinically acceptable indicators of a disease state or progression thereof. Amelioration and treatment can require the administration of more than one dose of a compound of formula (I) or (II), either alone or in conjunction with other therapeutic agents and interventions. Amelioration or treatment does not require that the disease or condition be cured.

As used herein, "prevention" is understood as to limit, reduce the rate or degree of onset, or inhibit the development of at least one sign or symptom of a disease or condition particularly in a subject prone to developing the disease or condition. For example, a subject having a mutation in a gene, such as the opsin gene, is likely to develop retinitis pigmentosa (RP). The age of onset of one or more symptoms of the disease can sometimes be determined by the specific mutation. Prevention can thus include the delay of onset of one or more signs or symptoms of RP and need not be prevention of appearance of at least one sign or symptom of the disease throughout the lifetime of the subject.

As used herein, "protecting" or "protection" of cells including normal cells, refers to any oxidative damage a cell can sustain, in particular, oxidative damage from environmental factors, for example, the sun, carcinogens; diseases, such as neurological diseases, cancer, drugs such as adriamycin and arsenic trioxide, diseases caused by organisms, such as viruses, bacteria and the like. Protecting against oxidative damage comprises preventing, inhibiting, reducing, reactive oxidation intermediates which cause damage to a cell.

The terms "therapeutically effective amount, "effective amount," and "effective dose" refer to that amount of a compound of formula (I) and (II) to produce the intended pharmacological, protective, therapeutic or preventive result. The pharmacologically effective amount may result in the prolonged survival, amelioration of one or more signs or symptoms of a disease or condition, or inhibition or reduction of cellular production of ROS in vivo or in vitro. For example, in the context of the treatment of an ocular disease or condition, a therapeutically effective amount preferably refers to the amount of a compound of formula (I or II) that decreases the loss of night vision, the loss of overall visual acuity, the loss of visual field, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more as compared to an untreated control subject over a defined period of time, e.g., 2 weeks, one month, 2 months, 3 months, 6 months, one year, 2 years, 5 years, or longer. More than one dose may be required to provide an effective dose.

II. Inventive Compounds

A first aspect of the present invention is directed to novel compositions of matter. In some embodiments, the compounds are represented by formula (I), as follows:

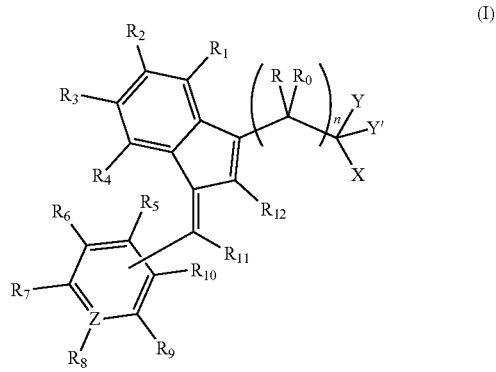

(I)

wherein: R, $R_0$, $R_1$, $R_2$, $R_3$, $R_4$, $R_{11}$, and $R_{12}$ are independently selected from hydrogen, alkyl, alkenyl, alkynyl, alkoxy, alkylmercapto, alkylsulfoxide, alkyl sulphone, hydroxy, amino, alkyamino, dialkylamino, azido, cyano, halogen, and substituted or unsubstituted aryl or substituted or unsubstituted aryl(alkyl)oxy;

wherein $R_5$, $R_6$, $R_7$, $R_8$, $R_9$ and $R_{10}$, if present, are independently selected from hydrogen, alkyl, alkenyl, alkynyl, alkoxy, alkylmercapto, alkylsulfoxide, alkyl sulphone, hydroxy, amino, alkyamino, dialkylamino, azido, cyano, halogen, oxide, and substituted or unsubstituted aryl or substituted or unsubstituted aryl(alkyl)oxy; or wherein any neighboring two of R to $R_{12}$ may form a saturated or unsaturated, optionally substituted carbocyclic or heterocyclic ring;

X represents hydrogen, hydroxyl, substituted or unsubstituted amino, substituted or unsubstituted alkoxyamino, substituted or unsubstituted alkyloxy, substituted or unsubstituted thiol, substituted or unsubstituted alkylmercapto, substituted or unsubstituted alkyl; or when Y and Y' together represent O, X represents a substituted amine or a group A-$(CH_2)_m$—$R_{13}$, wherein A represents O or N, $R_{13}$ is a saturated or unsaturated, substituted or unsubstituted carbocyclic or heterocyclic group containing at least one hetero atom which is nitrogen, oxygen, or sulfur, and wherein the substituents are independently selected from alkyl, alkoxy, alkylmercapto, alkylsulfoxide, alkylsulphone, cyano, halogen, hydroxy, amino, alkyamino, dialkylamino, azido, and substituted or unsubstituted benzyl, and when $R_{13}$ represents substituted or unsubstituted aryl, the aryl substituents may be alkyl, alkyloxyl, alkylmercapto, amino, hydroxyl or halogen; and wherein m is 0, 1 or 2;

Y and Y' are independently selected from hydrogen, hydroxyl, or wherein Y and Y' together may be a carbon, oxygen, sulfur, or a nitrogen atom;

Z represents carbon, nitrogen, oxygen or sulfur;

and n is 0, 1 or 2; or a pharmaceutically acceptable salt thereof.

In some embodiments, R and $R_0$ are each hydrogen. In some embodiments, at least one of $R_1$-$R_4$ is alkyloxy, e.g., methoxy, and in some other embodiments, $R_2$ is alkoxy or both $R_2$ and $R_3$ are alkyloxy. In some embodiments, $R_7$ is hydrogen or halogen, e.g., F or Cl. In some embodiments, at least one of $R_7$, $R_8$ and $R_9$ is alkyloxy, e.g., methoxy, and $R_8$ is a substituted aryl(alkyl)oxy group, wherein the substituent is alkyloxy, e.g., methoxy, and in some other embodiments, $R_7$ and $R_9$ are each alkoxy, and in yet other embodiments, each of $R_7$, $R_8$ and $R_9$ is alkyloxy. In some embodiments, $R_{11}$ is hydrogen and (as shown in formula (II)) $R_{12}$ is alkyl, e.g., methyl. In some embodiments, Y and Y' together represent oxygen; and X represents a substituted amine or a group A-$(CH_2)_m$—$R_{13}$, wherein A represents O or N, $R_{13}$ is a saturated or unsaturated, substituted or unsubstituted carbocyclic or heterocyclic group containing at least one hetero atom which is nitrogen, oxygen, or sulfur, and wherein the substituents are independently selected from alkyl, alkoxy, alkylmercapto, alkylsulfoxide, alkylsulphone, cyano, halogen, hydroxy, amino alkyamino, dialkylamino, azido, and when $R_{13}$ represents substituted or unsubstituted aryl, the aryl substituents may be alkyl, alkyloxy, alkylmercapto, amino, hydroxyl or halogen; and wherein m is 0, 1 or 2.

In some embodiments, Z represents carbon. In some embodiments, m is 0 or 1. In some embodiments, the carbocyclic ring is optionally substituted phenyl. In some embodiments, the heterocyclic ring is an optionally substituted, saturated or unsaturated 5/6-membered ring containing at least one S, N or O, e.g., pyridine, piperidine, piperazine, morpholine, pyrrole, pyrrolidine, imidazole, oxazole, and/or thiazole.

In some embodiments, the compounds of the present invention are represented by formula

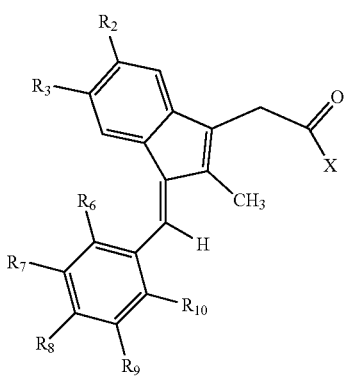

(II)

wherein R, $R_0$, $R_1$ and $R_4$ are each hydrogen;

$R_2$ and $R_3$ are selected from hydrogen, lower alkoxy, substituted or unsubstituted aryl(alkyl)oxy, provided that at least one of $R_2$ and $R_3$ is lower alkoxy or substituted or unsubstitutedaryl(alkyl)oxy, and in some embodiments, $R_2$ and $R_3$ are lower alkoxy or benzyloxy, and in some embodiments $R_2$ and $R_3$ are each lower alkoxy;

$R_5$ is not present, and $R_6$ and $R_{10}$ each represent hydrogen;

at least one of $R_7$, $R_8$ and $R_9$ is lower alkoxy or substituted or unsubstituted aryl(alkyl)oxy, and in some embodiments, at least two of $R_7$, $R_8$ and $R_9$ are lower alkoxy or substituted or unsubstituted aryl(alky)oxy, and in some embodiments, two of $R_7$, $R_8$ and $R_9$ are lower alkoxy and one of $R_7$, $R_8$ and $R_9$ is hydrogen, halogen (e.g., F) or amino or (di)alkylamino, and in some embodiments $R_7$ and $R_9$ are lower alkoxy, and $R_8$ is lower alkoxy, wherein the substituents are defined as per formula (I), and in some embodiments, each of $R_7$, $R_8$ and $R_9$ are lower alkoxy. In some embodiments, at least one of $R_2$, $R_3$, $R_7$, $R_8$ and $R_9$ is substituted or unsubstituted aryl(alkyl)oxy, e.g., benzyoxy, wherein the benzyloxy substituents include alkoxy (e.g., methoxy), alkyl, alkylamino, dialkylamino, acylamino, and halo;

$R_{11}$ represents hydrogen;

$R_{12}$ represents methyl; and

X represents hydroxyl or (as defined in formula (I)), -A-$(CH_2)_m$—$R_{13}$, wherein in some embodiments, A is O and m is 1.

Compounds of formula (I) and (II) can have one or more asymmetric carbons and thus such compounds are capable of existing as enantiomers or diastereomers. Unless otherwise specified, the present invention includes such enantiomers or diastereomers, including any racemates thereof. If desired, the separate enantiomers or diastereomers can be synthesized from appropriate chiral starting materials, or the racemates can be resolved by conventional procedures, which are well-known to those skilled in the art, such as chiral chromatography, fractional crystallization of diastereomers or diastereomeric salts, and the like. Certain compounds can exist as geometrical isomers, such as, for example, compounds with double-bonded substituents with geometrical isomers Z and E, and the present invention includes all such isomers, including certain isomers, for example, the Z isomers.

In some embodiments, the compound of formula (I) or (II) is in the form of a pharmaceutically acceptable salt. In some embodiments, the pharmaceutically acceptable salt is a sodium salt, a hydrochloride salt or a citric acid salt. In some embodiments, e.g., when Y, Y' and X form an ester group, the compound of formula (I) or (II) may be said to be in the form of a prodrug wherein the ester group is cleaved following administration.

In some embodiments, the compound is (Z)-2-(5,6-dimethoxy-2-methyl-1-(3,4,5-trimethoxybenzylidene)-1H-inden-3-yl)acetic acid ("compound 9"), or a pharmaceutically acceptable salt or prodrug thereof (wherein in the latter, the hydroxyl group is replaced by a substituted amine or a group A-$(CH_2)_m$—$R_{13}$ (as defined above).

In some other embodiments, compounds of formulas (I) and (II) (including prodrugs thereof) are as follows:

| Structure | IUPAC names |
|---|---|
| 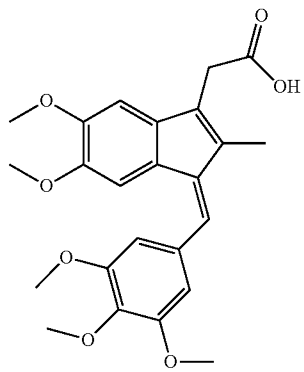 [SMILES: COc1cc2c(cc1OC)/C(=C\c1cc(OC)c(OC)c(OC)c1)C(C)=C2CC(=O)O] | (Z)-2-(5,6-dimethoxy-2-methyl-1-(3,4,5-trimethoxybenzylidene)-1H-inden-3-yl)acetic acid |
| 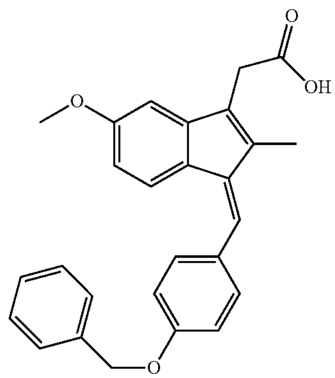 [SMILES: COc1ccc2c(c1)C(CC(=O)O)=C(C)/C2=C/c1ccc(OCc2ccccc2)cc1] | (Z)-2-(1-(4-(benzyloxy)benzylidene)-5-methoxy-2-methyl-1H-inden-3-yl)acetic acid |
| 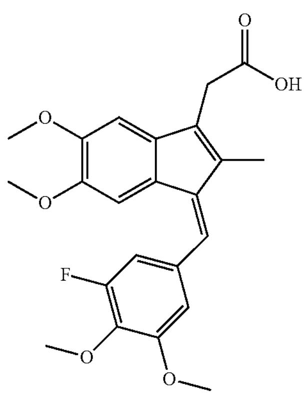 [SMILES: COc1cc2c(cc1OC)/C(=C\c1cc(F)c(OC)c(OC)c1)C(C)=C2CC(=O)O] | (Z)-2-(1-(3-fluoro-4,5-dimethoxybenzylidene)-5,6-dimethoxy-2-methyl-1H-inden-3-yl)acetic acid |
| 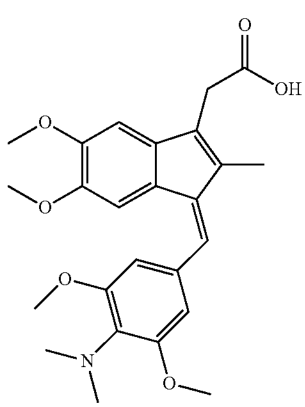 [SMILES: COc1cc2c(cc1OC)/C(=C\c1cc(OC)c(N(C)C)c(OC)c1)C(C)=C2CC(=O)O] | (Z)-2-(1-(4-(dimethylamino)-3,5-dimethoxybenzylidene)-5,6-dimethoxy-2-methyl-1H-inden-3-yl)acetic acid |

| Structure | IUPAC names |
|---|---|
| 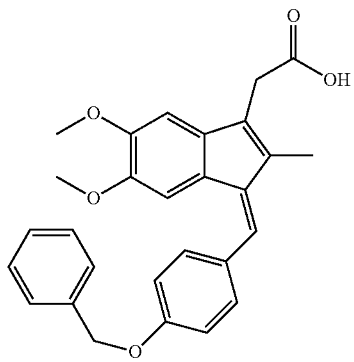 [SMILES: COc1cc2c(cc1OC)/C(=C\c1ccc(OCc3ccccc3)cc1)C(C)=C2CC(=O)O] | (Z)-2-(1-(4-(benzyloxy)benzylidene)-5,6-dimethoxy-2-methyl-1H-inden-3-yl)acetic acid |
| 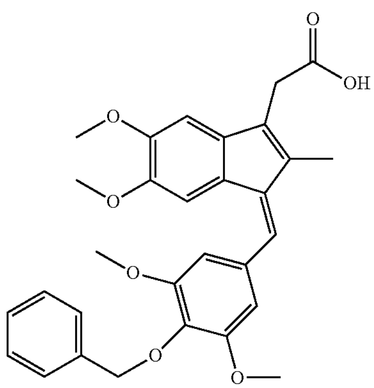 [SMILES: COc1cc2c(cc1OC)/C(=C\c1cc(OC)c(OCc3ccccc3)c(OC)c1)C(C)=C2CC(=O)O] | (Z)-2-(1-(4-(benzyloxy)-3,5-dimethoxybenzylidene)-5,6-dimethoxy-2-methyl-1H-inden-3-yl)acetic acid |
| 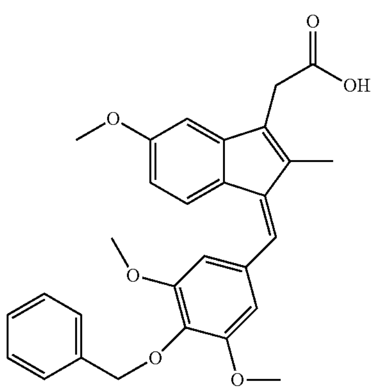 [SMILES: COc1ccc2c(c1)C(CC(=O)O)=C(C)/C2=C/c1cc(OC)c(OCc2ccccc2)c(OC)c1] | (Z)-2-(1-(4-(benzyloxy)-3,5-dimethoxybenzylidene)-5-methoxy-2-methyl-1H-inden-3-yl)acetic acid |
| 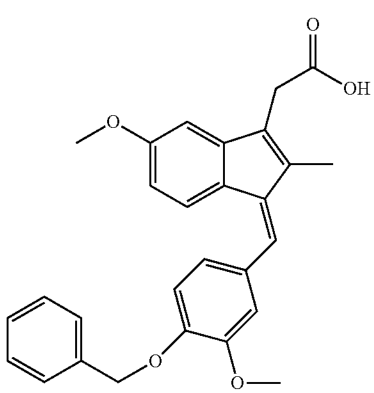 [SMILES: COc1ccc2c(c1)C(CC(=O)O)=C(C)/C2=C/c1ccc(OCc2ccccc2)c(OC)c1] | (Z)-2-(1-(4-(benzyloxy)-3-methoxybenzylidene)-5-methoxy-2-methyl-1H-inden-3-yl)acetic acid |

-continued

| Structure | IUPAC names |
|---|---|
| 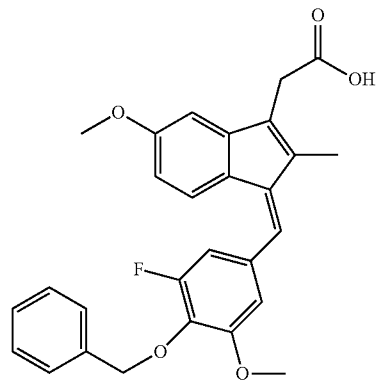 | (Z)-2-(1-(4-(benzyloxy)-3-fluoro-5-methoxybenzylidene)-5-methoxy-2-methyl-1H-inden-3-yl)acetic acid |
| 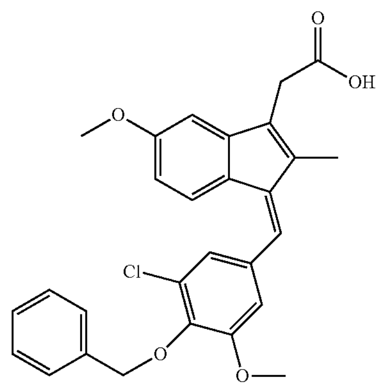 [SMILES: COc1ccc2c(c1)C(CC(=O)O)=C(C)/C2=C/c1cc(Cl)c(OCc2ccccc2)c(OC)c1] | (Z)-2-(1-(4-(benzyloxy)-3-chloro-5-methoxybenzylidene)-5-methoxy-2-methyl-1H-inden-3-yl)acetic acid |
| 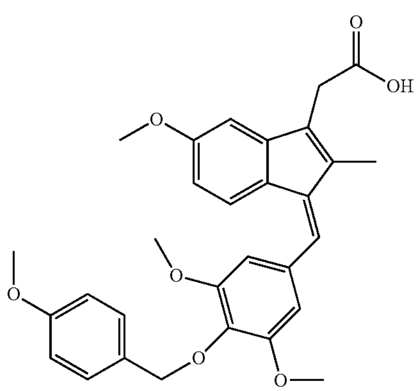 [SMILES: COc1ccc(COc2c(OC)cc(/C=C3/C(C)=C(CC(=O)O)c4cc(OC)ccc43)cc2OC)cc1] | (Z)-2-(1-(3,5-dimethoxy-4-((4-methoxybenzyl)oxy)benzylidene)-5-methoxy-2-methyl-1H-inden-3-yl)acetic acid |
| 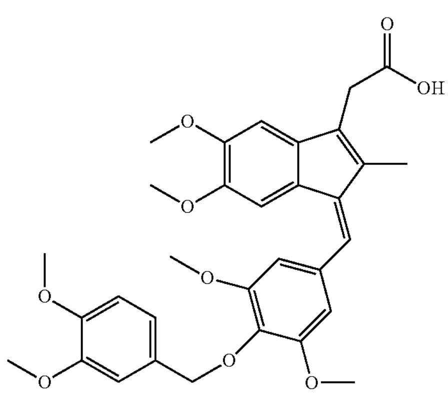 [SMILES: COc1ccc(COc2c(OC)cc(/C=C3/C(C)=C(CC(=O)O)c4cc(OC)c(OC)cc43)cc2OC)cc1OC] | (Z)-2-(1-(4-((3,4-dimethoxybenzyl)oxy)-3,5-dimethoxybenzylidene)-5,6-dimethoxy-2-methyl-1H-inden-3-yl)acetic acid |

| Structure | IUPAC names |
|---|---|
| 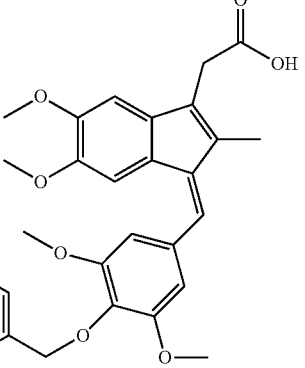 | (Z)-2-(1-(3,5-dimethoxy-4-((4-methoxybenzyl)oxy)benzylidene)-5,6-dimethoxy-2-methyl-1H-inden-3-yl)acetic acid |
| 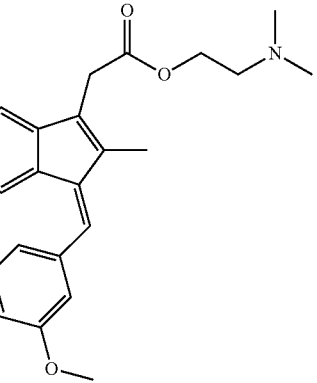 | 2-(dimethylamino)ethyl (Z)-2-(5,6-dimethoxy-2-methyl-1-(3,4,5-trimethoxybenzylidene)-1H-inden-3-yl)acetate |
| 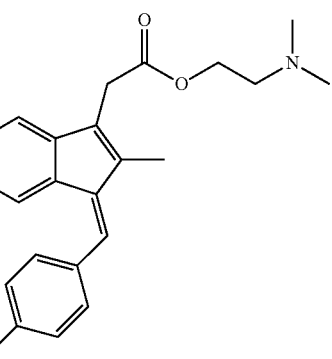 | 2-(dimethylamino)ethyl (Z)-2-(1-(4-(benzyloxy)benzylidene)-5-methoxy-2-methyl-1H-inden-3-yl)acetate |
| 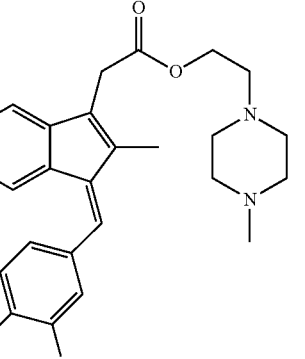 | 2-(4-methylpiperazin-1-yl)ethyl (Z)-2-(5,6-dimethoxy-2-methyl-1-(3,4,5-trimethoxybenzylidene)-1H-inden-3-yl)acetate |

| Structure | IUPAC names |
|---|---|
| 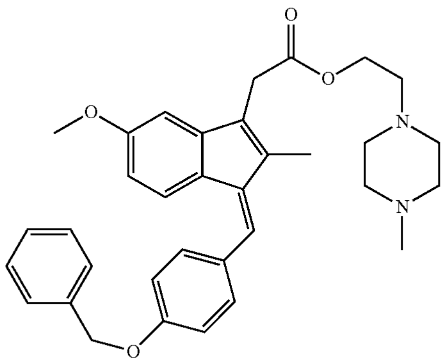 [SMILES: COc1ccc2c(c1)C(CC(=O)OCCN1CCN(C)CC1)=C(C)/C2=C/c1ccc(OCc2ccccc2)cc1] | 2-(4-methylpiperazin-1-yl)ethyl (Z)-2-(1-(4-(benzyloxy)benzylidene)-5-methoxy-2-methyl-1H-inden-3-yl)acetate |
| 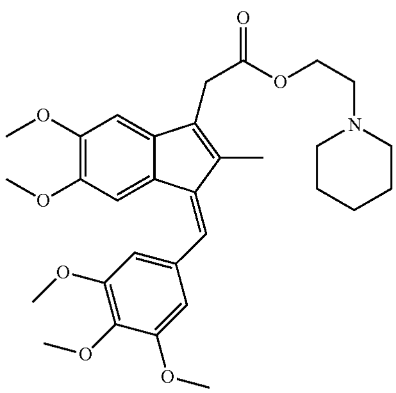 [SMILES: COc1cc2c(cc1OC)/C(=C\c1cc(OC)c(OC)c(OC)c1)C(C)=C2CC(=O)OCCN1CCCCC1] | 2-(piperidin-1-yl)ethyl (Z)-2-(5,6-dimethoxy-2-methyl-1-(3,4,5-trimethoxybenzylidene)-1H-inden-3-yl)acetate |
| 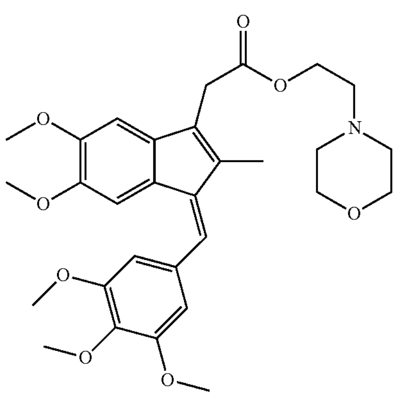 [SMILES: COc1cc2c(cc1OC)/C(=C\c1cc(OC)c(OC)c(OC)c1)C(C)=C2CC(=O)OCCN1CCOCC1] | 2-morpholinoethyl (Z)-2-(5,6-dimethoxy-2-methyl-1-(3,4,5-trimethoxybenzylidene)-1H-inden-3-yl)acetate |
| 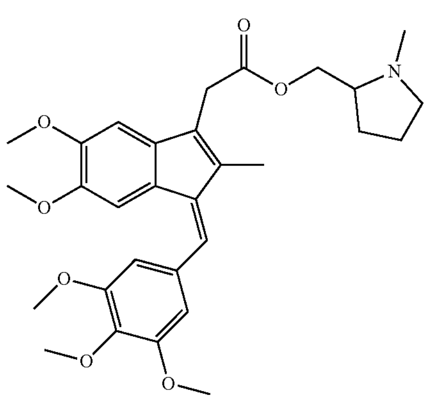 [SMILES: COc1cc2c(cc1OC)/C(=C\c1cc(OC)c(OC)c(OC)c1)C(C)=C2CC(=O)OCC1CCCN1C] | (1-methylpyrrolidin-2-yl)methyl (Z)-2-(5,6-dimethoxy-2-methyl-1-(3,4,5-trimethoxybenzylidene)-1H-inden-3-yl)acetate |

| Structure | IUPAC names |
| --- | --- |
| 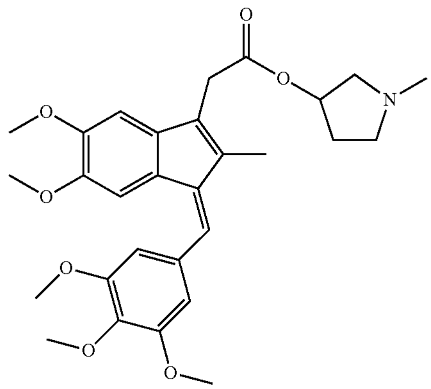 | 1-methylpyrrolidin-3-yl (Z)-2-(5,6-dimethoxy-2-methyl-1-(3,4,5-trimethoxybenzylidene)-1H-inden-3-yl)acetate |
| 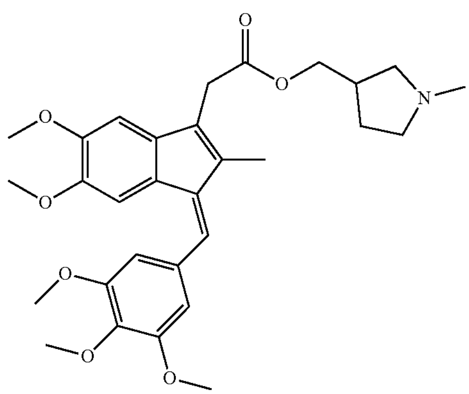 | (1-methylpyrrolidin-3-yl)methyl (Z)-2-(5,6-dimethoxy-2-methyl-1-(3,4,5-trimethoxybenzylidene)-1H-inden-3-yl)acetate |
| 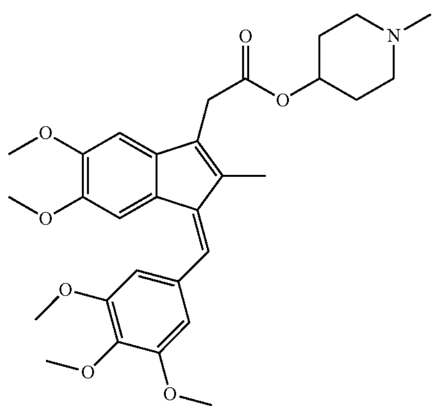 | 1-methylpiperidin-4-yl (Z)-2-(5,6-dimethoxy-2-methyl-1-(3,4,5-trimethoxybenzylidene)-1H-inden-3-yl)acetate |
| 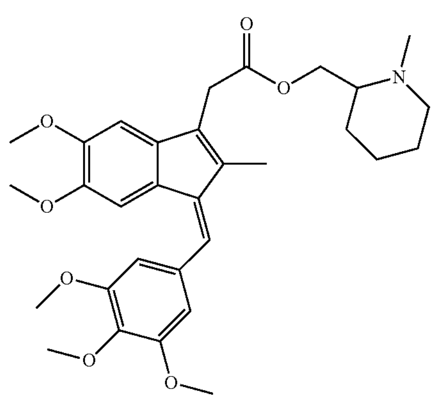 [SMILES: COc1cc2c(cc1OC)/C(=C\c1cc(OC)c(OC)c(OC)c1)C(C)=C2CC(=O)OCC1CCCCN1C] | (1-methylpiperidin-2-yl)methyl (Z)-2-(5,6-dimethoxy-2-methyl-1-(3,4,5-trimethoxybenzylidene)-1H-inden-3-yl)acetate |

| Structure | IUPAC names |
|---|---|
| 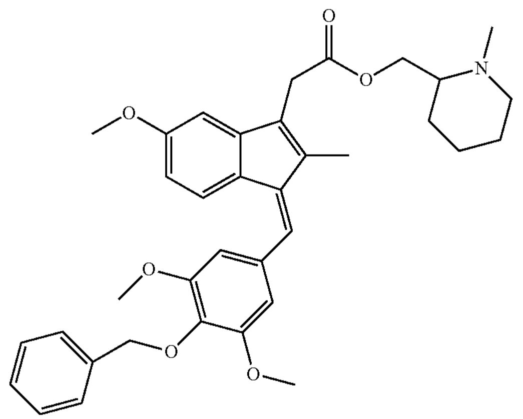 [SMILES: COc1ccc2c(c1)C(CC(=O)OCC1CCCCN1C)=C(C)/C2=C/c1cc(OC)c(OCc2ccccc2)c(OC)c1] | (1-methylpiperidin-2-yl)methyl (Z)-2-(1-(4-(benzyloxy)-3,5-dimethoxybenzylidene)-5-methoxy-2-methyl-1H-inden-3-yl)acetate |
| 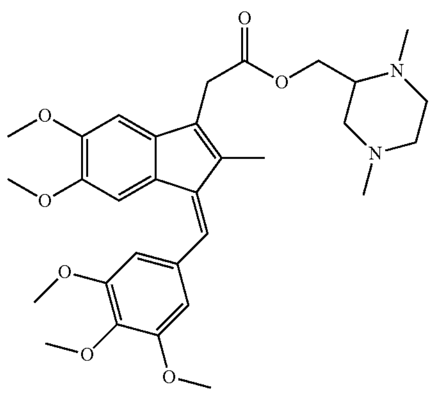 [SMILES: COc1cc2c(cc1OC)/C(=C\c1cc(OC)c(OC)c(OC)c1)C(C)=C2CC(=O)OCC1CN(C)CCN1C] | (1,4-dimethylpiperazin-2-yl)methyl (Z)-2-(5,6-dimethoxy-2-methyl-1-(3,4,5-trimethoxybenzylidene)-1H-inden-3-yl)acetate |
| 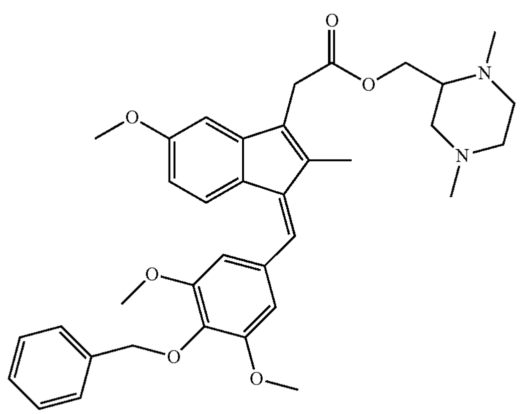 [SMILES: COc1ccc2c(c1)C(CC(=O)OCC1CN(C)CCN1C)=C(C)/C2=C/c1cc(OC)c(OCc2ccccc2)c(OC)c1] | (1,4-dimethylpiperazin-2-yl)methyl (Z)-2-(1-(4-(benzyloxy)-3,5-dimethoxybenzylidene)-5-methoxy-2-methyl-1H-inden-3-yl)acetate |
| 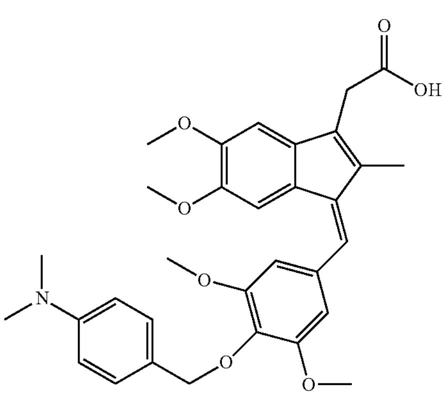 [SMILES: COc1cc2c(cc1OC)/C(=C\c1cc(OC)c(OCc3ccc(N(C)C)cc3)c(OC)c1)C(C)=C2CC(=O)O] | (Z)-2-(1-(4-((4-(dimethylamino)benzyl)oxy)-3,5-dimethoxybenzylidene)-5,6-dimethoxy-2-methyl-1H-inden-3-yl)acetic acid |

| Structure | IUPAC names |
|---|---|
| (structure) | (Z)-2-(1-(4-(benzo[d][1,3]dioxol-5-ylmethoxy)-3,5-dimethoxybenzylidene)-5,6-dimethoxy-2-methyl-1H-inden-3-yl)acetic acid |
| (structure) | (Z)-2-(1-(3,5-dimethoxy-4-((3,4,5-trimethoxybenzyl)oxy)benzylidene)-5,6-dimethoxy-2-methyl-1H-inden-3-yl)acetic acid |

III. Methods of Making the Inventive Compounds

In general, the compounds of formula (I) and (II) can be synthesized in accordance with the following reaction schemes.

Scheme I De nova Synthesis of Indene Analogs

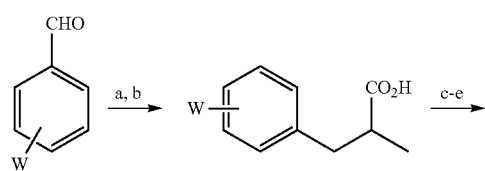

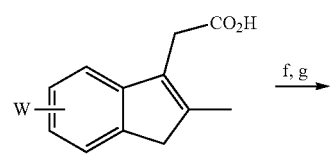

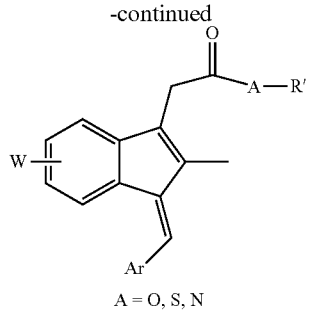

A = O, S, N a. (EtCO)$_2$O, EtCO$_2$Na, reflux; b. H$_2$, Pd—C, warm; c. PPA, 50-80° C.; d. NCCH$_2$CO$_2$H, AcOH, AcONH$_4$, toluene, Dean-Stark; e. KOH, H$_2$O; f. NaOCH$_3$, CH$_3$OH, ArCHO; g. (1) CDI, CH$_2$Cl$_2$, (2) R'OH, R'SH, OR R'NH$_2$.

Wherein: W represents R$_1$, R$_2$, R$_3$ and R$_5$.

A substituted benzaldehyde may be refluxed with propionic anhydride in the presence of sodium propionate. The resulting solid may be catalytically hydrogenated at 50° C. to obtain the substituted 2,3-dihydro-cinnamic acid. The acid may be treated with polyphosphoric acid (PPA) to afford a cyclic ketone. Treatment of the ketone with 2-cyanoacetic acid, followed by reaction with potassium hydroxide, will yield the substituted idenyl-acetic acid. Reaction of the acid with a substituted benzaldehyde in the presence of sodium methoxide in methanol will afford the benzylidene-indenylacetic acid. Treatment of the acid with carbonyl diimidazole (CDI) followed by adding a primary alcohol or an amine will yield the ester and amide. See, also e.g., U.S. Pat. No. 6,603,818.

IV. Pharmaceutical Compositions

In another aspect of the present invention, a compound of formula (I) or (II), or a pharmaceutically acceptable salt thereof, can be formulated into a composition, e.g., a pharmaceutical formulation or composition. In that respect, the present invention further provides a composition that includes an effective amount of compound of formula (I) or (II), which may be in the form of a pharmaceutically acceptable salt thereof, and a pharmaceutically acceptable carrier. The effective amount can include an amount that produces a protective, therapeutic or prophylactic response in a subject to whom a compound or composition of the present invention is administered.

Any suitable pharmacologically or physiologically acceptable carrier can be utilized; including for example, vehicles, solvents, adjuvants, excipients and diluents. One skilled in the art can easily determine the type of administration for the exact formulation or the composition based on the intended route of administration.

By way of example only, in the case of oral preparations, a compound of formulas (I) and (II) can be combined, if desired, with appropriate additives to make tablets, powders, granules, capsules, liquids, gels, syrups, slurries, solutions and suspensions.

Suitable additives for solid formulations such as these may include for example, lactose, mannitol, corn starch and potato starch. Suitable additives also can include binders, for example crystalline cellulose, cellulose derivatives, acacia, or gelatins; disintegrants, for example, corn starch, potato starch and sodium carboxymethylcellulose; and lubricants such as talc and magnesium stearate. Further additives such as, for example, diluents, buffering agents, moistening agents, preservatives, and/or flavoring agents, and the like, can be included in the compositions.

The compounds of formulas (I) and (II) can also be made into an aerosol formulation for administration by inhalation. Such aerosol formulations can be placed into pressurized acceptable propellants such as dichlorodifluoromethane, propane and nitrogen.

The compounds of formulas (I) and (II) can be formulated into suppositories by admixture with a variety of bases such as emulsifying bases or water-soluble bases. The suppository formulations can be administered rectally, and can include vehicles such as cocoa butter, carbowaxes, and polyethylene glycols, which melt at body temperature but are solid at room temperature.

In some embodiments, the compound of formula (I) or (II) may be formulated for ocular administration, such as an eye drop or eye ointment.

The compound of formula (I) or (II) may be added to a base solvent to give an aqueous solution or suspension and then the pH is adjusted within a range from 4 to 10, e.g., from 5 to 9. The eye drop may be subjected to a sterilization treatment so as to obtain a sterile product, and the sterilization treatment can be carried out in any stage of the production process. The concentration of the compound of formula (I) or (II) in the eye drop may be within a range from about 0.001 to about 5% (W/V), e.g., about 0.5 to about 1.0% (W/V). The dose may vary depending on the degree of symptoms and constitution of patients and the eye drop may be applied 1 to 4 times per day in an amount of several drops. This dose is merely a measure and can deviate from the above range according to the pathological conditions of the treatment.

To the eye drop, various additives such as buffering agents, isotonizing agents, antiseptics, pH adjustors, thickeners, chelating agents and, solubilizing agents may be appropriately added. Examples of the buffering agent include citrate buffering agent, tartaric acid buffering agent, acetate buffering agent and amino acid. Examples of the isotonizing agent include saccharides such as sorbitol, glucose and mannitol, polyhydric alcohols such as glycerin, polyethylene glycol and propylene glycol, and salts such as sodium chloride. Examples of the antiseptic include paraoxybenzoate esters such as methyl paraoxybenzoate and ethyl paraoxybenzote, benzyl alcohol, phenethyl alcohol, sorbic acid or salts thereof. Examples of the pH adjustor include phosphoric acid and sodium hydroxide. Examples of the thickener include hydroxyethyl cellulose, hydroxypropyl cellulose, methyl cellulose, hydroxypropylmethyl cellulose, carboxymethyl cellulose and salts thereof. Examples of the chelating agent include sodium edetate, sodium citrate and condensed sodium phosphate, and examples of the solubilizing agent include ethanol and polyoxyethylene hardened castor oil.

The eye ointment may be obtained by mixing the compound of formula (I) or (II) with an eye ointment base such as purified lanolin, white petrolatum, macrogol, plastibase or liquid paraffin, and is preferably subjected to a sterilization treatment so as to obtain a sterile product. The concentration of the phenylazole compounds of the present invention in the eye ointment is within a range from about 0.0001 to about 5% (W/V), and preferably from 0.5 to 1% (W/V). The dose varies depending on the degree of symptoms and constitution of patients and the eye ointment may be applied 1 to 4 times per day. This dose is merely a measure and can deviate from the above range according to the pathological conditions of the treatment.

Formulations suitable for topical administration include liquid or semi-liquid preparations suitable for penetration through the skin to the site where treatment is required, such as liniments, lotions creams, ointments or pastes, and drops.

Lotions of the present invention including those suitable for application to the skin or eye. An eye lotion may include a sterile aqueous solution, optionally containing a bactericide, and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may include hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

For parental administration, the compositions are preferably formulated in a sterilized pyrogen-free form. For injection, the agents of the invention may be formulated in aqueous solutions, preferably in physiologically compatible buffers such as Hanks's solution, Ringer's solution, or physiological saline buffer. Additionally, suspensions of the active compounds may be prepared as appropriate oily injections of the active compounds may be prepared as appropriate oily injection suspensions. Suitable lipophilic solvents or vehicles include fatty oils such as sesame oil, synthetic fatty acid esters, such as ethyl oleate or triglycerides, and liposomes. Aqueous injection suspensions may contain substances which increase the viscosity of the suspension, such as sodium carbomethyl cellulose, sorbitol, and dextran. Optionally, the suspension may also contain suitable stabilizers or agents which increase the solubility of the compounds to allow for the preparation of highly concentrated solutions.

The determination of the appropriate dose of a compound of formula (I) or (II) is well within the ordinary skill of the art, as are optimization of dosage and the formulation type for a given subject. Thus, for example, as described herein below, the compounds can be formulated for administration via any standard or medically accepted route. The effective amount and method of administration of compounds will vary based upon the sex, age, weight and disease stage of the subject, whether the administration is therapeutic or prophylactic, and other factors apparent to those skilled in the art. Those skilled in the art will derive appropriate dosages and schedules of administration to suit the specific circumstances and needs of the subject, e.g., dependent on the subject's weight, the severity of the affliction, the manner of administration and the judgment of the prescribing physician.

Although the exact dosage will be determined on a drug-by-drug basis, in most cases, some generalizations regarding the dosage can be made. The daily dosage regimen for an adult human patient may be, for example, a dose of between 1 mg and 500 mg, e.g., between about 1 mg and about 250 mg, e.g., about 150 to about 200 mg. In some embodiments, the oral dosage form is about 5 mg, 10 mg, 25 mg, 50 mg, 100 mg, 125 mg, 150 mg, 175 mg, 200 mg, 225 mg, 250 mg or 300 mg.

The term "unit dosage form" as used herein refers to physically discrete units suitable as unitary dosages for human and animal subjects, each unit containing a predetermined quantity of at least one compound of formula (I) or (II). The unit dosage can be determined by methods known to those of skill in the art, for example, by calculating the amount of active ingredient sufficient to produce the desired effect in association with a pharmaceutically acceptable carrier. The specifications for the unit dosage forms that can be used in accordance with the present invention depend on the particular effect to be achieved and the particular pharmacodynamics associated with the compound(s) in the individual subject.

The compositions may, if desired, be presented in a pack or dispenser device which may contain one or more unit dosage forms containing the active ingredient. The pack or dispenser device may be accompanied by instructions for administration.

V. Methods of Use

Normal metabolism produces free radical molecules. Free radicals are atoms or molecules which have at least one unpaired electron in the outer orbital. These radicals are the same as generated by external radiation and include hydrogen peroxide and superoxide. Mitochondria are the main source of oxygen free radicals under normal conditions. Free radicals can react with any biological molecule (proteins, lipids, sugars, DNA) altering its structure and often also its function. Therefore living organisms are provided with a rich system of antioxidant defenses whose main purpose is to prevent the free radicals attack to other molecules. Antioxidants can also be supplied in the form of nutrition (e.g., phytochemicals in fruit and vegetables). Oxidative stress arises from an imbalance of these radicals and antioxidants as a result of which unneutralized radicals damage DNA and other macromolecules. Oxidative stress occurs to some extent in everyone. However, levels of oxidative stress and ROS that substantially exceed the mean plus a standard deviation (relative to a population of disease-free individuals) can be recognized as a cause of a multitude of diseases, may make the body more susceptible to other disease initiating factors, inhibit endogenous defenses and repair processes, and enhance disease progression.

In general, the compounds and compositions of the present invention may be used to protect cells including normal cells against oxidative damage. Such uses or methods include: preventing or inhibiting ischemic/reoxygenation injury in a patient, particularly in the myocardium and central nervous system; preserving organs for transplant in an anoxic, hypoxic, or hyperoxic state prior to transplant; protecting normal tissues from free radical-induced damage consequent to exposure to ionizing radiation and/or chemotherapy; protecting cells and tissues from free radical-induced injury consequent to exposure to xenobiotic compounds which form free radicals; enhancing cryopreservation of cells, tissues, organs, and organisms by increasing viability of recovered specimens; prophylactic administration to prevent cellular senescence, cataract formation, formation of malondialdehyde adducts, HIV pathology and macromolecular crosslinking, such as collagen crosslinking; protection of normal cells from damage caused by environmental factors e.g., rays from the sun, such as for example, ultra violet rays and gamma rays, and carcinogens; protection of normal cells in a subject from damage caused by aging, including age-related immune deficiency and premature aging disorders, cancer, cardiovascular disease, cerebrovascular disease, radiation injury, alcohol-mediated damage (including Wernicke-Korsakoff s syndrome), inflammatory and auto-immune disease, drug toxicity, amyloid disease, overload syndromes (iron, copper, etc.), multi-system organ failure, and endotoxemia/sepsis; and enhancing wound recovery.

Thus, in some embodiments, a compound of formula (I) or (II) is administered to a subject undergoing or expected to undergo: an ischemic episode, such as a myocardial infarction, cerebral ischemic event, transplantation operation, open heart surgery, elective angioplasty, coronary artery bypass surgery, brain surgery, renal infarction, traumatic hemorrhage, and tourniquet application; antineoplastic or antihelminthic chemotherapy employing a chemotherapeutic agent which generates free radicals; endotoxic shock or sepsis; exposure to ionizing radiation; exposure to exogenous chemical compounds which are free radicals or produce free radicals; thermal or chemical burns or ulcerations; hyperbaric oxygen; and apoptosis of a predetermined cell population (e.g., lymphocyte apoptosis).

In some embodiments, the present invention provides methods for the prevention, inhibition, amelioration, or treatment of a non-cancerous disease or condition associated with oxidative stress (and related to excess ROS production) in a subject by administration of a prophylactically therapeutically effective amount of a compound of formula (I) or (II) to the subject. Examples of conditions associated with oxidative stress include reperfusion injury, wound healing, toxic hepatitis, viral hepatitis, chronic organ disease (e.g., chronic lung disease, chronic obstructive pulmonary disease, chronic viral hepatitis, chronic renal disease, chronic pancreatitis, chronic prostatitis, chronic inherited bleeding disorders (e.g., hemophilia, von Willebrand disease), and chronic bone disease (e.g., osteogenesis imperfect, Paget's disease), oxidative stress from dialysis, renal toxicity, kidney failure, ulcerative colitis, bacterial infection, viral infections, upper respiratory tract diseases, oxidative stress due to sun damage, eczema, atopic dermatitis, polymyositis, dermatitis, herpetiformis, and pre-cancerous conditions.

Certain of the conditions characterized by oxidative stress fall within the cardiovascular group, including myocardial ischemia, myocardial infarction, cardiopulmonary inflammatory disorders; and heart failure (including chronic and congestive heart failure).

Another group of conditions characterized by oxidative stress fall within the cerebrovascular and neurologic group, including stroke, cerebral ischemia, retinal ischemia, post-surgical cognitive dysfunctions (e.g., following bypass surgery), peripheral neuropathy spinal cord injury, head injury and surgical trauma, and neurodegenerative disorders including Alzheimer's, dementia and Parkinson's disease.

In some embodiments, a compound of formula (I) or (II) is used to treat ischemia. Ischemia refers to a disorder caused by an imbalance between supply and demand of oxygen to tissue, usually caused by a reduction in blood flow to the tissue. Organs such as the heart and brain are most vulnerable to ischemia due to their high extraction of oxygen. Reperfusion is the process of restoring blood flow to the tissue. Ischemia and reperfusion result in different damage to the tissues deprived of oxygen. The reduction of blood flow decreases the production of high energy phosphates. During ischemia, cells are damaged and their mitochondria becomes less efficient. Restarting blood flow after more than about ten minutes of ischemia is typically more damaging than the ischemia itself because the damaged cells produce large amounts of reactive oxygen species.

Subjects at risk of ischemia include those having previously had heart disease, those having elevated biochemical markers of the disease (e.g., protein C), those identified as having blockage of blood vessels by angioplasty or MRI imaging, and those undergoing a surgical procedure requiring temporary obstruction of blood vessels.

In some embodiments, a compound of formula (I) or (II) is used to treat stroke. Stroke is a sudden loss of brain function resulting from interference with the blood supply to the central nervous system. Acute stroke can be classified either as ischemic (80% of stroke cases), which can be further classified to extra-cranial embolism and intracranial thrombosis, or a hemorrhagic stroke (20% of stroke cases), which can be further classified to intracerebral hemorrhage and subarachnoid hemorrhage. Ischemic stroke accounts for 70 to 80% of all strokes and hemorrhagic stroke accounts for the remainder. Free radicals play an important role in the pathogenesis of stroke. In most cases, subjects at risk of stroke can be determined by presence of one, and usually at least two of the following risk factors: high blood pressure, heart disease, high cholesterol levels, sleep apnea, previous occurrence of stroke, smoking, excessive alcohol consumption and excessive weight.

Another group of diseases characterized by oxidative stress and involving inflammatory and/or autoimmune components includes diabetes; renal disease; pre-menstrual syndrome; asthma; rheumatoid arthritis; osteoarthritis, muscle fatigue; irritable bowel syndrome, inflammatory bowel disease and intermittent claudication.

Another group of diseases characterized by oxidative stress fall within the group of dermatologic conditions, including, prevention and protecting skin tissue against age-related damage or damage resulting from insults such as harmful ultraviolet (UV) radiation, stress and fatigue.

In yet further embodiments, various retinal diseases characterized by oxidative stress may be treated with the compounds of formula (I) or (II).

Photoreceptor outer segments contain rhodopsin as well as the highest content of DHA of any cell type. In contact with the photoreceptor tips is a monolayer of cells, the retinal pigment epithelium (RPE), derived from neuroepithelium. These cells are the most active phagocytes of the body. In a daily cycle, they engulf and phagocytize the distal tips of photoreceptor outer segments, thereby participating in rod outer segment renewal in a process that is balanced by addition of new membrane to the base of the outer segments. The conservation of DHA in photoreceptors is supported by retrieval through the interphotoreceptor matrix, which supplies the fatty acid for the biogenesis of outer segments. See, Stinson, et al., J. Lipid Res. 32:2009-2017 (1991).

RPE cells also perform several other functions, including transport and reisomerization of bleached visual pigments, and contribute to the maintenance of the integrity of the blood-outer retinal barrier. Retinal detachment or trauma triggers dysfunctions in the RPE cells that lead to the onset and development of proliferative vitreoretinopathy.

RPE cells are essential for photoreceptor cell survival. When RPE cells are damaged or die, photoreceptor function is impaired, and the cells die as a consequence. Thus, oxidative stress-mediated injury and cell death in RPE cells impair vision, particularly when the RPE cells of the macula are affected. The macula is responsible for visual acuity.

In summary, retinal photoreceptors are packed with mitochondria and have extremely high metabolic activity and oxygen consumption. Since production of ROS the electron transport chain is a major source of oxidative stress, photoreceptors are challenged under normal circumstances. In patients with retinitis pigmentosa (RP), one of a number of different mutations causes death of rods which drastically reduces oxygen consumption and elevates oxygen levels in the outer retina. Prolonged exposure to high levels of oxygen causes progressive oxidative damage to cones, Shen et al., J. Cell Physiol. 203:457-464 (2005), and their gradual death results in progressive constriction of visual fields and eventual blindness.

Thus, in some embodiments, a compound of formula (I) or (II) is used to treat retinitis pigmentosa (RP). RP is a type of progressive retinal dystrophy, a group of inherited disorders in which abnormalities of the photoreceptors (rods and cones) or the retinal pigment epithelium (RPE) of the retina lead to progressive visual loss. Affected individuals first experience defective dark adaptation or nyctalopia (night blindness), followed by reduction of the peripheral visual field (known as tunnel vision) and, sometimes, loss of central vision late in the course of the disease.

The diagnosis of retinitis pigmentosa relies upon documentation of progressive loss in photoreceptor function by electroretinography (ERG) and visual field testing. The mode of inheritance of RP is determined by family history. At least 35 different genes or loci are known to cause "nonsyndromic RP" (RP that is not the result of another disease or part of a wider syndrome). RP is commonly caused by a mutation in the opsin gene, but can be caused by mutations in a number of other genes expressed systemically or exclusively in the eye involved in the visual cycle.

Oxidative damage has also been implicated in another highly prevalent eye disease, age-related macular degeneration (AMD). Thus, in some embodiments, a compound of formula (I) or (II) is used to treat AMD.

Yet other ocular diseases and conditions that may be treated with compounds of the present invention include both wet and dry, diabetic retinopathy, Lebers optic neuropathy, and optic neuritis.

Compounds of formula (I) or (II) may also be useful in the treatment of subjects who are at risk or predisposed to cancer. These subjects that would be the recipients of such treatment have pre-cancerous conditions, which are known in the art as a group of disorders that have a malignant predisposition. Representative examples of pre-cancerous conditions that may be treated in accordance with the present inventive compounds include adenomas/polyps in subjects with familial adenomatous polyposis (Gardner's syndrome), sporadic adenomatous polyposis, or precancerous conditions associated with the hereditary non-polyposis colon cancer (Lynch syndrome), inflammatory bowel disease, or Crohn's disease. Examples of precancerous conditions of other tissues include cervical dysplasia or squamous intraepithelial lesion (e.g., diagnosed by a pap smear), prostatic intraepithelial neoplasia (PIN), superficial bladder cancer, also known as transitional cell carcinoma in situ, precancerous lesions of the breast, precancerous lesions of the lungs, actinic keratosis, Barrett's esophagus, precancerous melanoma moles, precancerous conditions of the uterus/vulva, precancerous conditions of the ovary, atrophic gastritis, precancerous conditions of the oral cavity, general dysplastic conditions, squamous metaplasia, intraepithelial neoplasia, and precancerous conditions in the head or neck.

The compounds of the present invention can, for example, be administered by any medically accepted route, including, for example, ophthalmically (e.g., intraocularly, intravitreally, subretinally), parenterally (e.g., intravenously, intraarterially, subdermally, intraperitoneally, intramuscularly, or subcutaneously) or orally, topically, buccally, nasally, transmucosally, or directly to a diseased organ, e.g., surgically or by catheter.

Compositions of the invention can also be administered in vitro to a cell (for example, to prevent oxidative damage during ex vivo cell manipulation, for example of organs used for organ transplantation or in in vitro assays) by simply adding the composition to the fluid in which the cell is contained.

It will be appreciated that an agent (e.g., (Z)-2-(5,6-dimethoxy-2-methyl-1-(3,4,5-trimethoxybenzylidene)-1H-inden-3-yl)acetic acid, or a pharmaceutically acceptable salt or prodrug thereof) or composition, as described herein, can be administered in combination with one or more additional pharmaceutical agents (e.g., therapeutically and/or prophylactically active agents), which are different from the agent or composition and may be useful as, e.g., combination therapies. The agents or compositions can be administered in combination with additional pharmaceutical agents that improve their activity (e.g., activity (e.g., potency and/or efficacy) in treating a disease in a subject in need thereof, in preventing a disease and/or injurious incident in a subject in need thereof, in reducing the risk of developing a disease in a subject in need thereof, etc. in a subject or cell. In certain embodiments, a pharmaceutical composition described herein including an agent (e.g., (Z)-2-(5,6-dimethoxy-2-methyl-1-(3,4,5-trimethoxybenzylidene)-1H-inden-3-yl) acetic acid, or a pharmaceutically acceptable salt or prodrug thereof) described herein and an additional pharmaceutical agent shows a synergistic effect that is absent in a pharmaceutical composition including one of the agent and the additional pharmaceutical agent, but not both.

In some embodiments of the disclosure, a therapeutic or prophylactic agent distinct from a first therapeutic or prophylactic agent of the disclosure is administered prior to, in combination with, at the same time (i.e., co-administered), or after administration of the agent of the disclosure. In some embodiments, the second therapeutic agent is selected from the group consisting of aspirin, a blood pressure medication, a type II diabetes medication, an mTOR inhibitor and/or other chemotherapeutic agent, etc.

The agent or composition can be administered concurrently with (i.e., co-administered), prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the agent or composition described herein in a single dose or administered separately in different doses. The particular combination to employ in a regimen will take into account compatibility of the agent described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, aspirin, blood pressure medications, type II diabetes medications, mTOR inhibitors, other anti-cancer agents, immunomodulatory agents, anti-proliferative agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the agents described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Dosages for a particular agent of the instant disclosure may be determined empirically in individuals Who have been given one or more administrations of the agent.

Administration of an agent of the present disclosure can be continuous or intermittent, depending, for example, on the recipient's physiological condition, whether the purpose of the administration is therapeutic or prophylactic, and other factors known to skilled practitioners. The administration of an agent may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the instant disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

VI. Kits

The instant disclosure also provides kits containing agents of this disclosure for use in the methods of the present disclosure. Kits of the instant disclosure may include one or more containers comprising a purified agent (e.g., (Z)-2-(5,6-dimethoxy-2-methyl-1-(3,4,5-trimethoxybenzylidene)-1H-inden-3-yl)acetic acid, or a pharmaceutically acceptable salt or prodrug thereof) of this disclosure and/or may contain agents for identifying a subject at elevated risk for an ischemic event. In some embodiments, the kits further include instructions for use in accordance with the methods of this disclosure. In some embodiments, these instructions comprise a description of administration of the agent to treat, prevent and/or diagnose, e.g., a risk factor that predisposes a subject to an ischemic event, according to any of the methods of this disclosure. In some embodiments, the instructions comprise a description of how to detect a subject at elevated risk of an ischemic event of a tissue, optionally of the heart, brain, kidneys, liver or lung. The kit may further comprise a description of selecting an individual suitable for treatment based on identifying whether that subject has an ischemia-predisposing risk factor(s).

The instructions generally include information as to dosage, dosing schedule, and route of administration for the intended treatment. The containers may be unit doses, bulk packages (e.g., multi-dose packages) or subunit doses. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating or preventing, e.g., an ischemic event and/or the negative effects attributable to an ischemic event, in a subject. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). In certain embodiments, at least one active agent in the composition is (Z)-2-(5,6-dimethoxy-2-methyl-1-(3,4,5-trimethoxybenzylidene)-1H-inden-3-yl)acetic acid, or a pharmaceutically acceptable salt or prodrug thereof. The container may further comprise a second pharmaceutically active agent. Kits may optionally provide additional components such as buffers and interpretive information. Normally, the kit comprises a container and a label or package insert(s) on or associated with the container.

WORKING EXAMPLES

The present invention is now described in terms of the following non-limiting examples.

Example 1

Materials and Methods

Chemical synthesis of Compound 9: 3,4-Dimethoxybenzaldehyde was treated with propionic anhydride and sodium propionate at 130° C. for 36 h to give (Z)-3-(3,4-dimethoxyphenyl)-2-methylacrylic acid as a colorless solid. Catalytic hydrogenation at 40 psi afforded 3-(3,4-dimethoxyphenyl)-2-methylpropanoic acid as colorless oil. 5,6-Dimethoxy-2-methyl-2,3-dihydro-1H-inden-1-one was obtained by treating the oil with polyphosphoric acid (PPA) at 50° C. for 20 min, followed by a standard purification procedure; the ketone was refluxed with 2-cyanoacetic acid, acetic acid and ammonium chloride in toluene for 36h, followed by hydrolysis with potassium hydroxide in 60% of ethanol to give 2-(5,6-dimethoxy-2-methyl-1H-inden-3-yl)acetic acid. Reaction of the acid with 3,4,5-trimethoxybenzaldehyde and methoxide in methanol at 85° C. overnight afforded 2-(5,6-dimethoxy-2-methyl-1-(3,4,5-trimethoxybenzyl)-1H-inden-3-yl)acetic acid (Compound 9) as a yellow solid.

Chemical synthesis of Compound 10: 4-Dimethoxybenzaldehyde was treated with propionic anhydride and sodium propionate at 130° C. for 36 h to give (Z)-3-(4-methoxyphenyl)-2-methylacrylic acid as a colorless solid. Catalytic hydrogenation at 40 psi afforded 3-(4-methoxyphenyl)-2-methylpropanoic acid as colorless oil. 6-Methoxy-2-methyl-2,3-dihydro-1H-inden-1-one was obtained by treating the oil with polyphosphoric acid (PPA) at 50° C. for 20 min, followed by a standard purification procedure; the ketone was refluxed with 2-cyanoacetic acid, acetic acid and ammonium chloride in toluene for 36h, followed by hydrolysis with potassium hydroxide in 60% of ethanol to give 2-(5-methoxy-2-methyl-1H-inden-3-yl)acetic acid. Reaction of the acid with 4-benzyloxy-benzaldehyde and methoxide in methanol at 85° C. overnight afforded (Z)-2-(1-(4-(benzyloxy)benzylidene)-5-methoxy-2-methyl-1H-inden-3-yl)acetic acid (Compound 10) as a yellow oil.

Cultured cells and reagents: Retinal pigmented epithelium cells (ARPE-19) were obtained from American Type Culture Collection (ATCC, Manassas, Va.) and cultured at 37° C. in 5% $CO_2$. All chemicals were purchased from Sigma unless specified.

Cell viability assay: Cells were cultured and assayed for cell viability essentially as described previously (14). ARPE-19 cells were plated at 10,000 cells per well in a 96-well plate. The cells were grown for 18-20 hours, the medium discarded in aseptic conditions and replaced with fresh culture medium containing the indicated drug concentration. The plates were incubated for 24 hours at 37° C. in a 5% CO$_2$ incubator in the presence of sulindac or Compound 9. To examine the treatment effects on oxidative damage to RPE cells, cells were washed and incubated in media without serum with various concentrations of tert-butyl hydroperoxide (TBHP) for an additional 24h. The culture medium was then discarded and the cells were thoroughly rinsed in PBS. Cell viability was determined by using the Cell Titer 96 Aqueous One Cell Proliferation Assay (Promega) according to the manufacturer's instructions. The assay utilizes a tetrazolium compound that is converted into a water-soluble formazan by the action of cellular NADH oxidase activity in metabolically active cells. The formazan was quantified by measuring the absorbance at 490 nm using a colorimetric microtiter plate reader (SpectraMax Plus; Molecular Devices).

PDE Assay

PDE activity was measured using the IMAP fluorescence polarization PDE assay (Molecular Devices) in which the binding of hydrolyzed fluorescent cyclic nucleotide substrate to the IMAP reagent increases fluorescence polarization. Each well of a 96-well nonbinding plate contained 0.25 mg/mL of recombinant enzyme preparations. Enzymes were incubated with COMPOUND 9 or vehicle (DMSO) for 30 min at 30° C. before the addition of a substrate mixture containing 25 nmol/L of fluorescein-cGMP. The DMSO final concentration for each experiment was 2%. After 90 min of incubation at 30° C., the reaction was terminated by the addition of binding reagent. The maximum Fluorescence polarization was measured using a Synergy4 (BioTek) plate reader.

COX Assay

Compounds were assayed for cyclooxygenase (COX) inhibition using the COX Fluorescent Inhibitor Screening Kit from Cayman Chemical (Item #: 700100). Briefly, COX enzyme (ovine COX-1 or human recombinant COX-2) diluted in 1× reaction buffer is incubated with the compound or DMSO control for 20 min at 25° C. in a half-area 96-well black microplate. Background wells are also included that contained no enzyme. Added to each well were heme B, to ensure enzyme activity, and 10-acetyl-3,7-dihydroxyphenoxazine (ADHP) assay reagent. After the 20 min incubation, arachidonic acid (AA) substrate was added to all wells. As shown by the schematic diagram below, active COX enzyme converts AA to hydroperoxy endoperoxide (PGG$_2$). Catalyzed by the secondary peroxidase activity of COX, ADHP can react with PGG$_2$ to form a highly fluorescent compound, resorufin. Fluorescence was measured with a 530-450 nm excitation wavelength and a 585-595 nm emission wavelength. Decreased fluorescence relative to the DMSO control indicates COX inhibition. See, also, Piazza G A, Keeton A B, Tinsley H N, Gary B D, Whitt J D, Mathew B, Thaiparambil J, Coward L, Gorman, G, Li Y, Sani B, Hobrath J V, Maxuitenko Y Y and Reynolds R C. A Novel Sulindac Derivative That Does Not Inhibit Cyclooxygenases, but Inhibits Colon Tumor Cell Growth and Induces Apoptosis with Antitumor Activity. Cancer Prevention Research 2009; 2: 572-580.

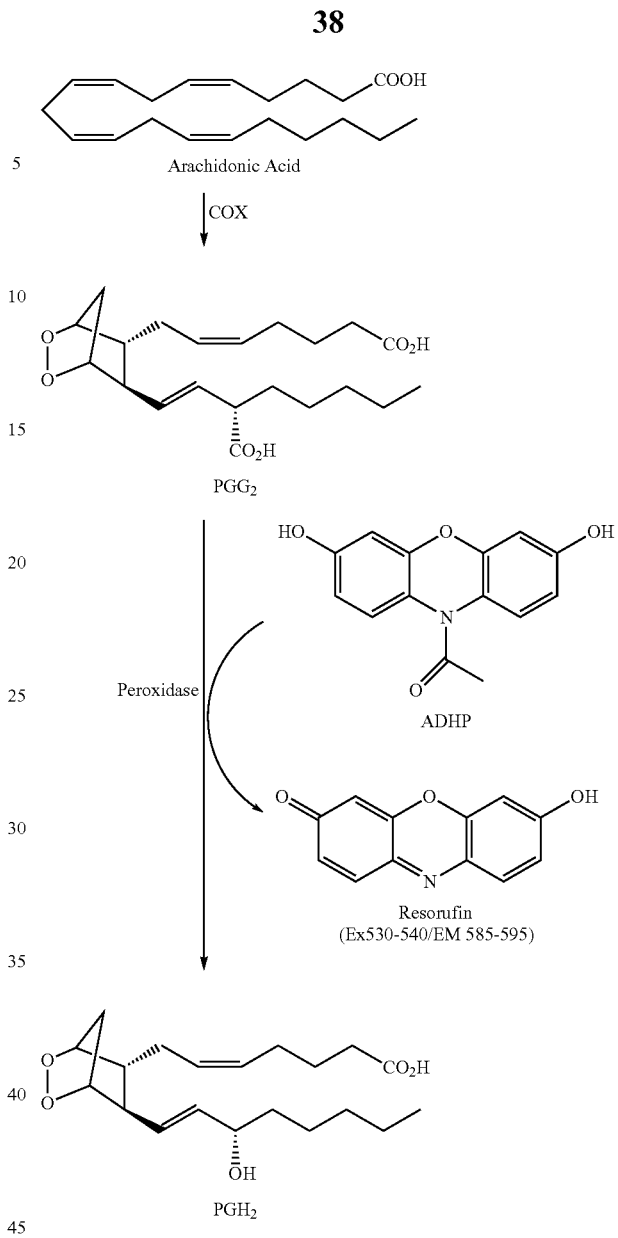

Langendorff Model

The ex vivo Langendorff procedure is a well-established preparation used to investigate heart physiology, ischemia/reperfusion injury, and other cardiovascular insults (23, 24; also see, e.g., reference 22). Sprague Dawley rats (275-325g) were administered either no drug or Compound 9 daily (at 0.7 mg/kg) for a total of two days (two administrations in total). Forty-eight hours after the start of drug exposure, hearts were removed and exposed to 45 min no flow ischemia and 2 h reperfusion in the Langendorff model (hearts were first equilibrated in KHB buffer for 10 min and then subjected to 45 min ischemia followed by 2 h reperfusion with KHB buffer), in the absence of drug.

Cell Death and Viability Assays

In LDH and TTC assays for the Langendorff Preparation, coronary effluent samples (500 μL) from the Langendorff preparation were obtained upon attachment of excised heart, every 15 min before ischemia, immediately after 45 min ischemia, and at 15 min intervals during reperfusion. LDH was measured (using a Cytotox-96 nonradioactive cytotoxicity assay kit (Promega), with the absorbance read at 490 nm). Immediately upon completion, the heart was sliced into 2-mm cross-sectional pieces and slices were incubated for 30 min with 1% 2,3,5-triphenyl tetrazolium chloride (TTC) stain in Krebs-Henseleit buffer (KHB) (pH=7.4) at 37° C. to distinguish between viable (red) and nonviable (white) tissue. Tissue slices were stored overnight in 10% formaldehyde before measurement of infarct size using NIH-Image J software.

Statistical Analysis

Data were analyzed using two tailed T-test or ANOVA using Graph pad prism software. Data are expressed as mean ±standard error (SE) with statistical significance set at p<0.05.

Example 2

Identification and Initial Evaluation of Indene Derivatives

Sulindac is a known NSAID that has been shown to have anti-cancer activity in experimental rodent models of tumorigenesis and is effective for the treatment of precancerous colonic adenomas in patients with familial adenomatous polyposis (15-17). However, sulindac, like other NSAIDs, has gastrointestinal and other toxicities resulting from COX inhibition that may limit their long-term use for cancer chemoprevention or other diseases. To develop safer and more efficacious derivatives, previous studies have focused primarily on synthesizing derivatives that have reduced COX inhibitory activity and improve potency to inhibit tumor cell growth (18, 19). As shown previously, sulindac can also protect normal cells against oxidative damage by initiating a protective preconditioning response (9, 10) that is independent of its COX inhibitory activity. Since the protective effect observed with sulindac using cells in culture required relatively high concentrations of the drug (10), there has been concern about possible long term toxicity related to its COX inhibitory activity.

We initiated a screen of a library of indene derivatives to identify novel compounds that are: 1) more potent than sulindac in protecting normal cells against oxidative damage; and 2) have lower or substantially lack COX inhibitory activity. In the present studies, a series of compounds were identified as having the ability to protect RPE cells against oxidative damage using tert-butyl hydroperoxide (TBHP), an organic peroxide, as an oxidizing agent (10).

The structures and names of the compounds screened, and the assay results, are shown in the following table.

| Compound | Structure | Cyto-protective activity* | IUPAC names |
|---|---|---|---|
| 1 | 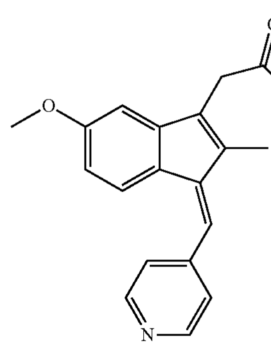 | inactive | sodium (Z)-2-(1-(4-(dimethylamino)benzylidene)-5-fluoro-2-methyl-1H-inden-3-yl)acetate |
| 2 | 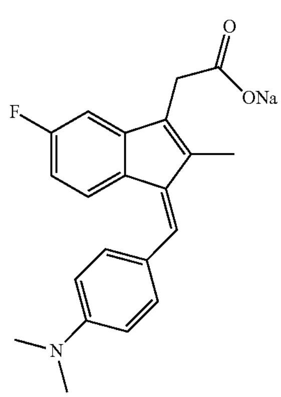 | inactive | sodium (Z)-2-(1-(4-(dimethylamino)benzylidene)-5-fluoro-2-methyl-1H-inden-3-yl)acetate |

-continued

| Compound | Structure | Cyto-protective activity* | IUPAC names |
|---|---|---|---|
| 3 | 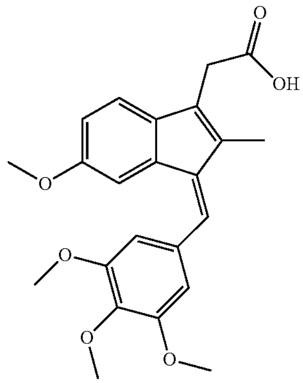 [SMILES: COc1ccc2c(c1)/C(=C\c1cc(OC)c(OC)c(OC)c1)C(C)=C2CC(=O)O] | inactive | (Z)-2-(6-methoxy-2-methyl-1-(3,4,5-trimethoxybenzylidene)-1H-inden-3-yl)acetic acid |
| 4 | 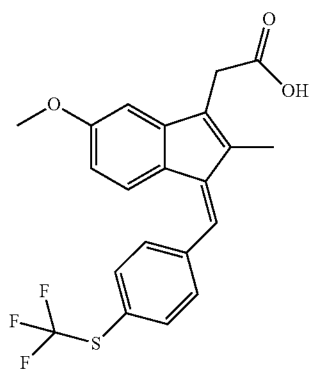 [SMILES: COc1ccc2c(c1)C(CC(=O)O)=C(C)/C2=C/c1ccc(SC(F)(F)F)cc1] | inactive | (Z)-2-(5-methoxy-2-methyl-1-(4-((trifluoromethyl)thio)benzylidene)-1H-inden-3-yl)acetic acid |
| 5 | 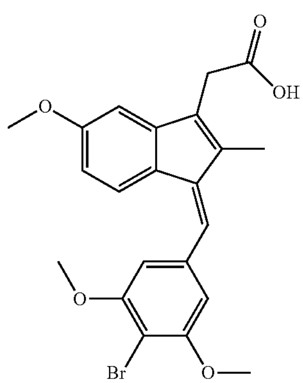 | inactive | (Z)-2-(1-(4-bromo-3,5-dimethoxybenzylidene)-5-methoxy-2-methyl-1H-inden-3-yl)acetic acid |
| 6 | 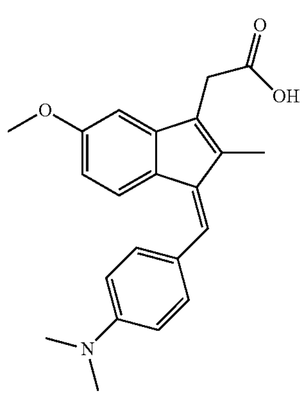 [SMILES: COc1ccc2c(c1)C(CC(=O)O)=C(C)/C2=C/c1ccc(N(C)C)cc1] | inactive | (Z)-2-(1-(4-(dimethylamino)benzylidene)-5-methoxy-2-methyl-1H-inden-3-yl)acetic acid |

-continued

| Compound | Structure | Cyto-protective activity* | IUPAC names |
|---|---|---|---|
| 7 | 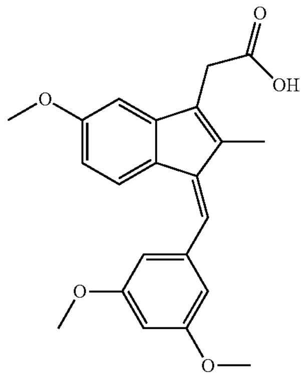 [SMILES: COc1cc(/C=C2/C(C)=C(CC(=O)O)c3cc(OC)ccc32)cc(OC)c1] | inactive | (Z)-2-(1-(3,5-dimethoxybenzylidene)-5-methoxy-2-methyl-1H-inden-3-yl)acetic acid |
| 8 | 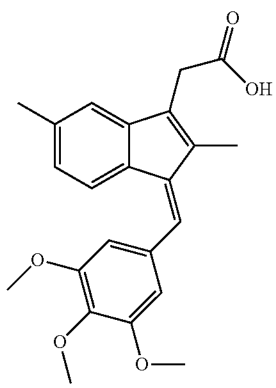 [SMILES: COc1cc(/C=C2/C(C)=C(CC(=O)O)c3cc(C)ccc32)cc(OC)c1OC] | inactive | (Z)-2-(2,5-dimethyl-1-(3,4,5-trimethoxybenzylidene)-1H-inden-3-yl)acetic acid |
| 9 | 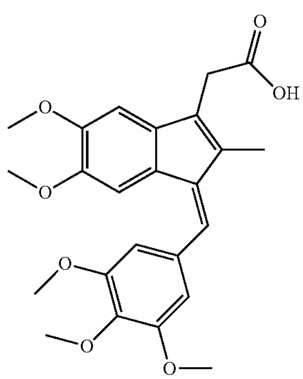 [SMILES: COc1cc2c(cc1OC)/C(=C\c1cc(OC)c(OC)c(OC)c1)C(C)=C2CC(=O)O] | active | (Z)-2-(5,6-dimethoxy-2-methyl-1-(3,4,5-trimethoxybenzylidene)-1H-inden-3-yl)acetic acid |
| 10 | 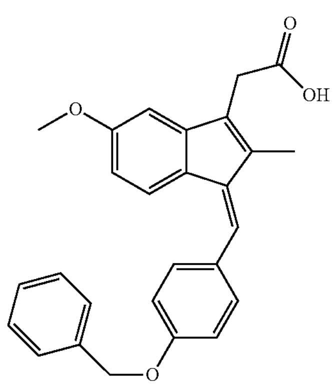 [SMILES: COc1ccc2c(c1)C(CC(=O)O)=C(C)/C2=C/c1ccc(OCc2ccccc2)cc1] | active | (Z)-2-(1-(4-(benzyloxy)benzylidene)-5-methoxy-2-methyl-1H-inden-3-yl)acetic acid |

-continued

| Compound | Structure | Cyto-protective activity* | IUPAC names |
|---|---|---|---|
| 11 | 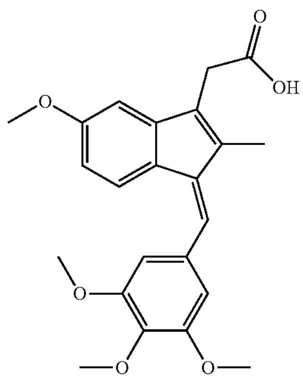 [SMILES: COc1ccc2c(c1)C(CC(=O)O)=C(C)/C2=C/c1cc(OC)c(OC)c(OC)c1] | inactive | (Z)-2-(5-methoxy-2-methyl-1-(3,4,5-trimethoxybenzylidene)-1H-inden-3-yl)acetic acid |
| 12 | 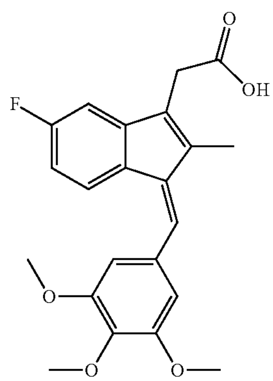 [SMILES: COc1cc(/C=C2/C(C)=C(CC(=O)O)c3cc(F)ccc32)cc(OC)c1OC] | inactive | (Z)-2-(5-fluoro-2-methyl-1-(3,4,5-trimethoxybenzylidene)-1H-inden-3-yl)acetic acid |
| 13 | 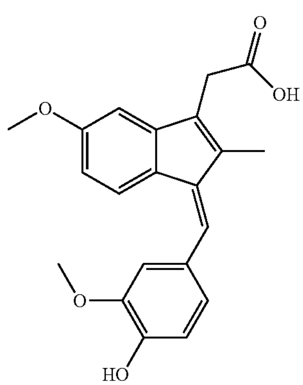 [SMILES: COc1ccc2c(c1)C(CC(=O)O)=C(C)/C2=C/c1ccc(O)c(OC)c1] | inactive | (Z)-2-(1-(4-hydroxy-3-methoxybenzylidene)-5-methoxy-2-methyl-1H-inden-3-yl)acetic acid |
| 14 | 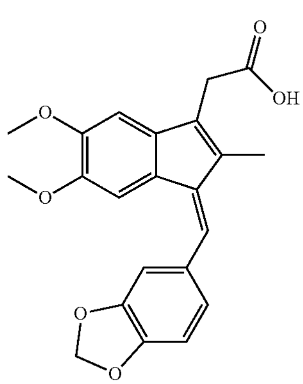 [SMILES: COc1cc2c(cc1OC)/C(=C\c1ccc3c(c1)OCO3)C(C)=C2CC(=O)O] | inactive | (Z)-2-(1-(benzo[d][1,3]dioxol-5-ylmethylene)-5,6-dimethoxy-2-methyl-1H-inden-3-yl)acetic acid |

-continued

| Compound | Structure | Cyto-protective activity* | IUPAC names |
|---|---|---|---|
| 15 | 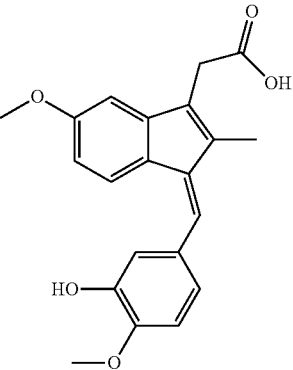 [SMILES: COc1ccc2c(c1)C(CC(=O)O)=C(C)/C2=C/c1ccc(OC)c(O)c1] | inactive | (Z)-2-(1-(3-hydroxy-4-methoxybenzylidene)-5-methoxy-2-methyl-1H-inden-3-yl)acetic acid |
| 16 | 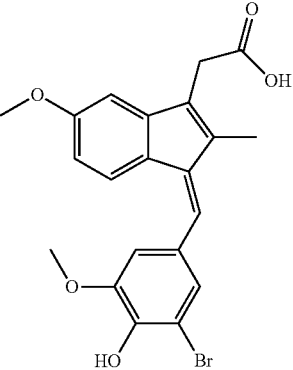 | inactive | (Z)-2-(1-(3-bromo-4-hydroxy-5-methoxybenzylidene)-5-methoxy-2-methyl-1H-inden-3-yl)acetic acid |
| 17 | 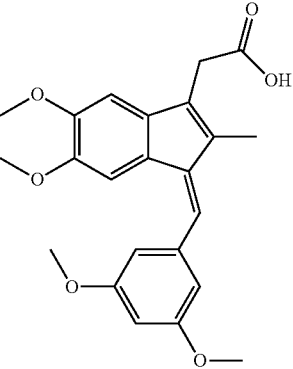 [SMILES: COc1cc(/C=C2/C(C)=C(CC(=O)O)c3cc(OC)c(OC)cc32)cc(OC)c1] | inactive | (Z)-2-(1-(3,5-dimethoxybenzylidene)-5,6-dimethoxy-2-methyl-1H-inden-3-yl)acetic acid |
| 18 | 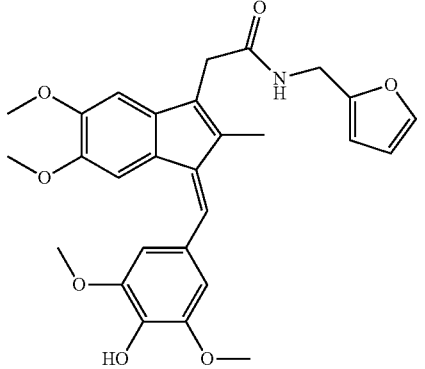 [SMILES: COc1cc2c(cc1OC)/C(=C\c1cc(OC)c(O)c(OC)c1)C(C)=C2CC(=O)NCc1ccco1] | inactive | (Z)-N-(furan-2-ylmethyl)-2-(1-(4-hydroxy-3,5-dimethoxybenzylidene)-5,6-dimethoxy-2-methyl-1H-inden-3-yl)acetamide |

-continued

| Compound | Structure | Cyto-protective activity* | IUPAC names |
|---|---|---|---|
| 19 | 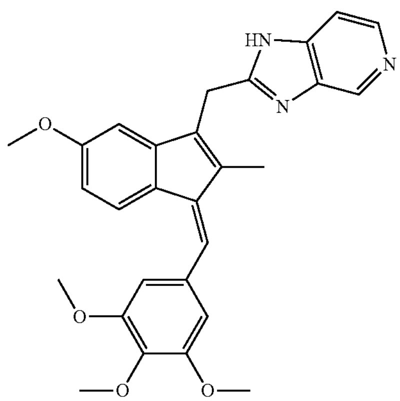 [SMILES: COc1ccc2c(c1)C(Cc1nc3cnccc3[nH]1)=C(C)/C2=C/c1cc(OC)c(OC)c(OC)c1] | inactive | (Z)-2-((5-methoxy-2-methyl-1-(3,4,5-trimethoxybenzylidene)-1H-inden-3-yl)methyl)-1H-imidazo[4,5-c]pyridine |
| 20 | 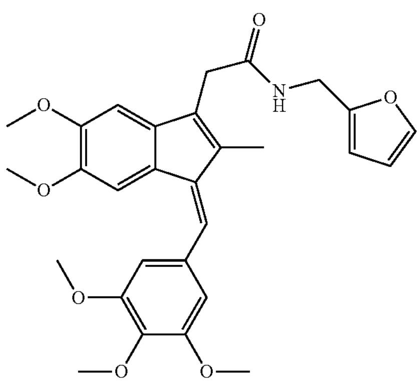 [SMILES: COc1cc2c(cc1OC)/C(=C\c1cc(OC)c(OC)c(OC)c1)C(C)=C2CC(=O)NCc1ccco1] | inactive | (Z)-2-(5,6-dimethoxy-2-methyl-1-(3,4,5-trimethoxybenzylidene)-1H-inden-3-yl)-N-(furan-2-ylmethyl)acetamide |
| 21 | 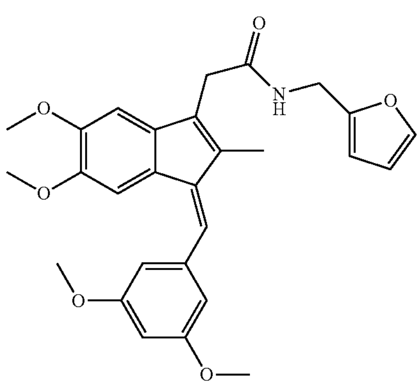 [SMILES: COc1cc(/C=C2/C(C)=C(CC(=O)NCc3ccco3)c3cc(OC)c(OC)cc32)cc(OC)c1] | inactive | (Z)-2-(1-(3,5-dimethoxybenzylidene)-5,6-dimethoxy-2-methyl-1H-inden-3-yl)-N-(furan-2-ylmethyl)acetamide |
| 22 | 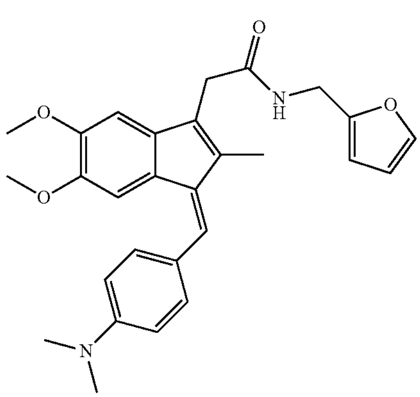 [SMILES: COc1cc2c(cc1OC)/C(=C\c1ccc(N(C)C)cc1)C(C)=C2CC(=O)NCc1ccco1] | inactive | (Z)-2-(1-(4-(dimethylamino)benzylidene)-5,6-dimethoxy-2-methyl-1H-inden-3-yl)-N-(furan-2-ylmethyl)acetamide |

| Compound | Structure | Cyto-protective activity* | IUPAC names |
|---|---|---|---|
| 23 | 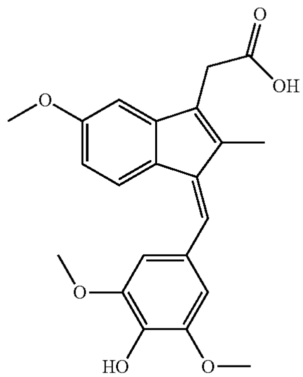 [SMILES: COc1ccc2c(c1)C(CC(=O)O)=C(C)/C2=C/c1cc(OC)c(O)c(OC)c1] | inactive | (Z)-2-(1-(4-hydroxy-3,5-dimethoxybenzylidene)-5-methoxy-2-methyl-1H-inden-3-yl)acetic acid |

*active = more active than Sulindac
inactive = less active than Sulindac

Figure 2:
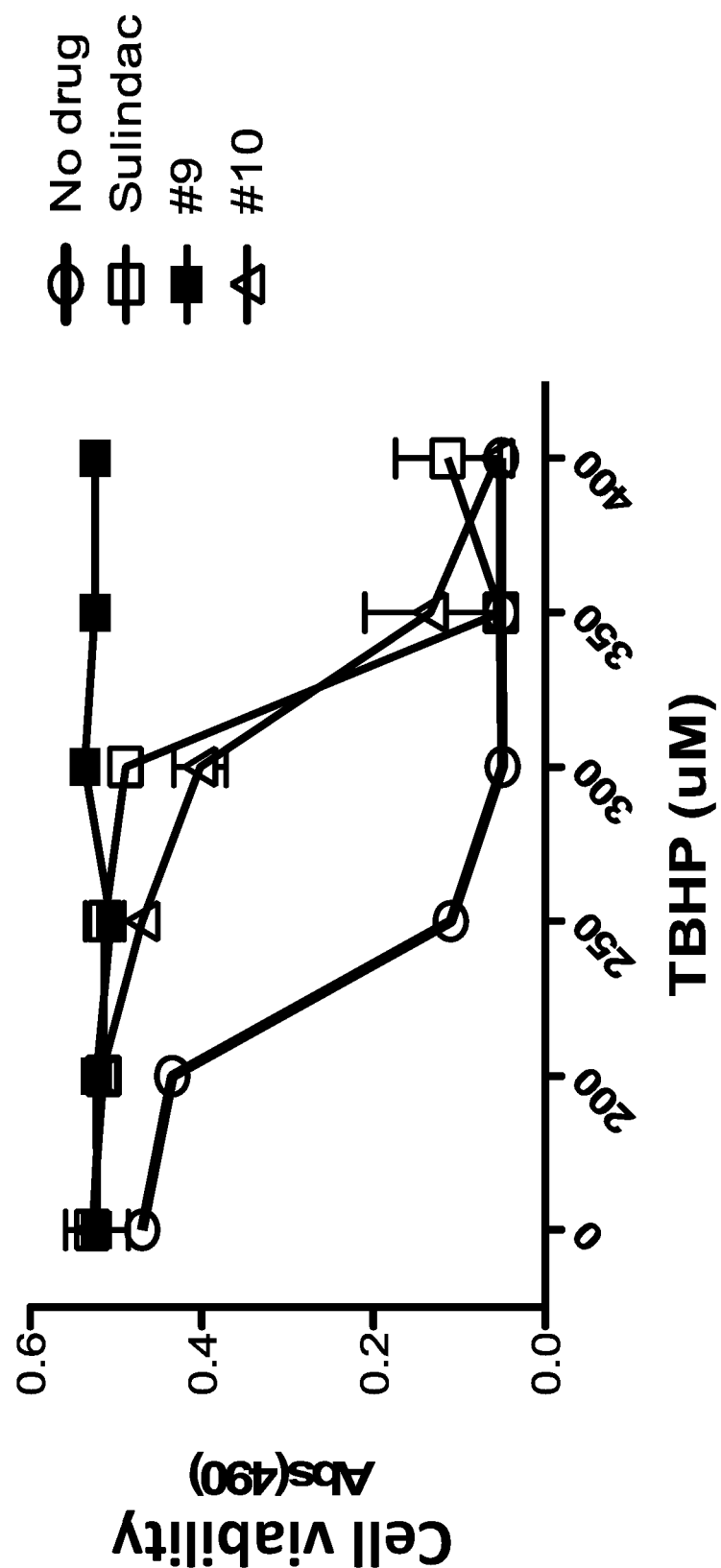
FIG. 2 shows protection of RPE cells against oxidative damage from TBHP by sulindac, Compound 9 and Compound 10. Sulindac was tested at a concentration of 200 while inventive Compounds 9 and 10 were tested at a concentration of 25 µM.
Figure 3:
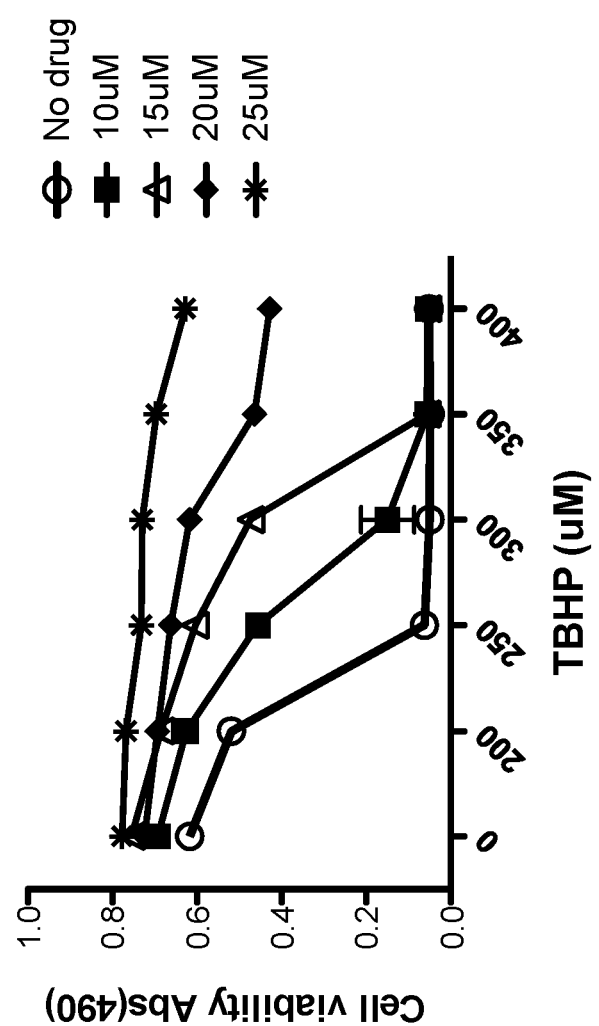
FIG. 3 shows concentration-dependent protection of RPE cells against oxidative damage from TBHP by Compound 9.

As shown in FIG. 2, Compound 9 (25 μM) provided complete protection of RPE cells from TBHP treatment up to TBHP concentrations of 400 μM, whereas sulindac (200 μM) was no longer protective at TBHP concentrations above 300 μM. Compound 10 was equally effective as sulindac but was more potent, being effective at an 8× lower concentration of 25 μM. Compound 9 was found to be effective at concentrations as low as 20× relative to sulindac at a concentration of 10 μM (FIG. 3).

Figure 4B:
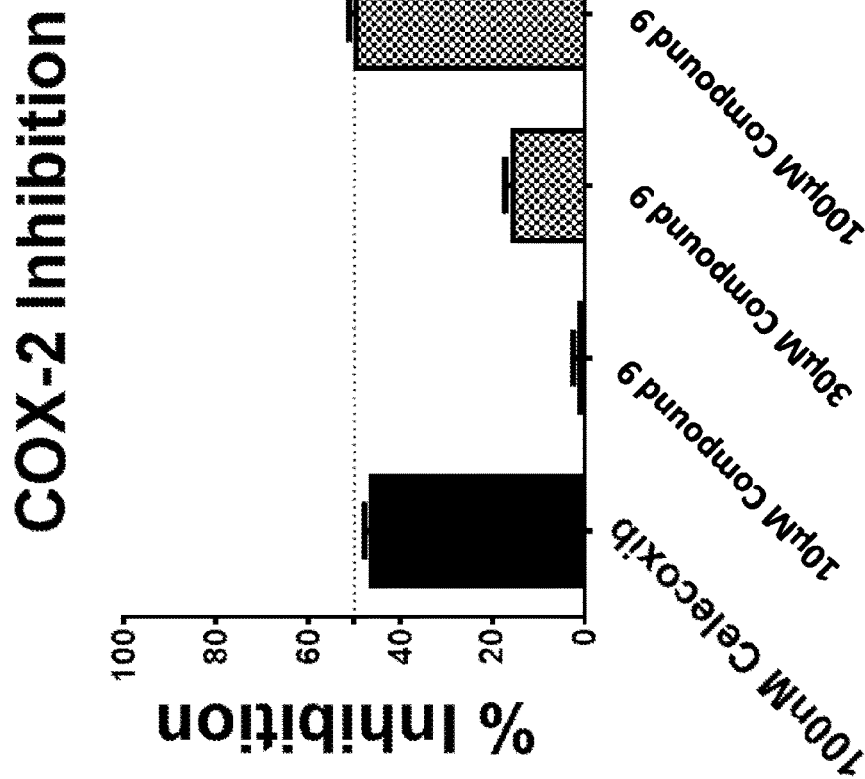
FIG. 4B shows that Compound 9 is approximately 1000× less potent than the known COX-2 inhibitor, celecoxib.
Figure 4A:
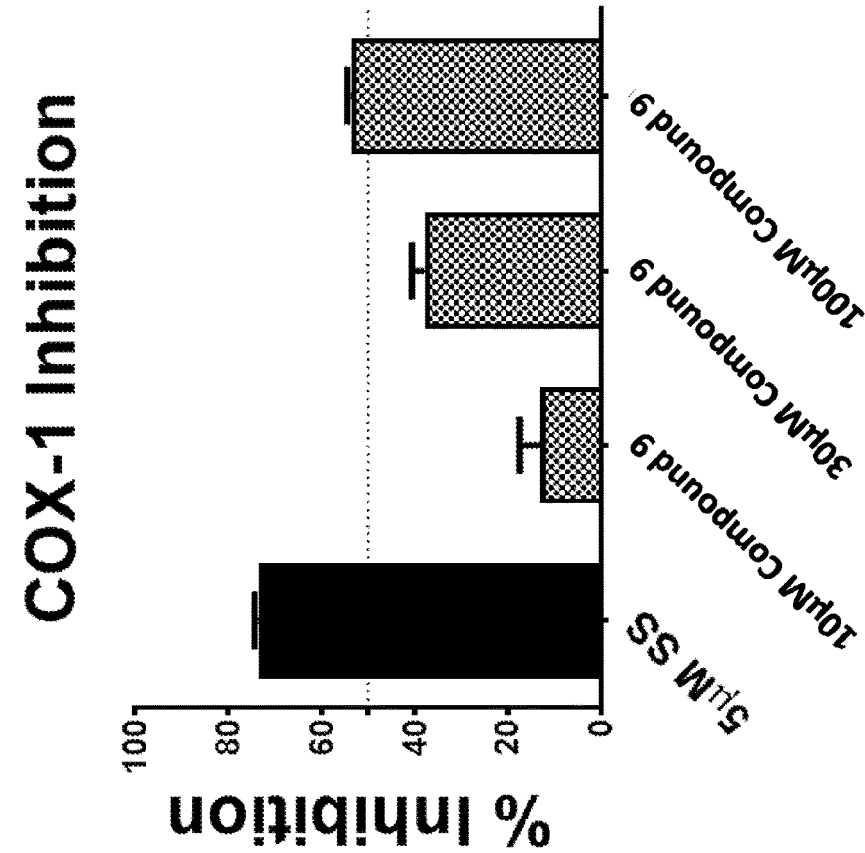
FIG. 4A shows that Compound 9 is at least 20× less potent than the known COX-1 inhibitor, sulindac sulfide (SS).

To determine if the cytoprotective activity of Compound 9 might involve COX-1 and/or COX-2 inhibition, the compound was tested for COX inhibitory activity in enzymatic assays. FIG. 4A shows that with respect to COX-1 inhibition, Compound 9 is least 20× less potent than the known COX-1 inhibitor, sulindac sulfide (SS). FIG. 4B shows that with respect to COX-2 inhibition, Compound 9 is approximately 1000× less potent than the known COX-2 inhibitor, celecoxib. These results show that Compound 9 essentially lacks pharmacologically significant COX-1 or COX-2 inhibitory activity.

Both the COX inhibitory sulfide and non-COX inhibitory sulfone metabolites of sulindac have been reported to inhibit cGMP degrading phosphodiesterases (PDE) with selectivity for PDE isozymes that hydrolyze cGMP. PDE inhibition results in elevated intracellular levels of cGMP and activation of protein kinase G (PKG). Inhibition of PDE5 and PDE10 inhibition may be responsible for the anticancer activity of sulindac by a mechanism involving the suppression of cytoplasmic/nuclear levels of β-catenin and inhibition of the TCF transcription factor, which mediates transcription of multiple proteins, including cell cycle regulatory and pro-survival genes such as cyclin D and survivin (20, 21). To determine if the cytoprotective activity of Compound 9 requires cGMP PDE inhibition, the effect of Compound 9 on the enzymatic activity of recombinant PDE isozymes was measured in enzymatic assays.

As shown in FIG. 5, Compound 9 inhibits PDE5 (FIG. 5A) and PDE10 (FIG. 5B) with IC50 values of about 32 μM and 7 μM, respectively, which are within the same concentration range required for cytoprotection of RPE cells exposed to oxidative damage by THBP. The PDE isozyme selectivity of Compound 9 was also determined by testing the sensitivity of PDE isozymes 1-11 (except PDE6). As shown in FIG. 5C, Compound 9 (25 μM) was most active against PDE5 and 10, although there was lower inhibitory effects on other cGMP PDE isozymes, including PDE 1, 2, 3 and 11. These results suggest that the elevation of cGMP by Compound 9, leading to increased activity of PKG, could be responsible for the cytoprotective activity of Compound 9.

Figure 6C:
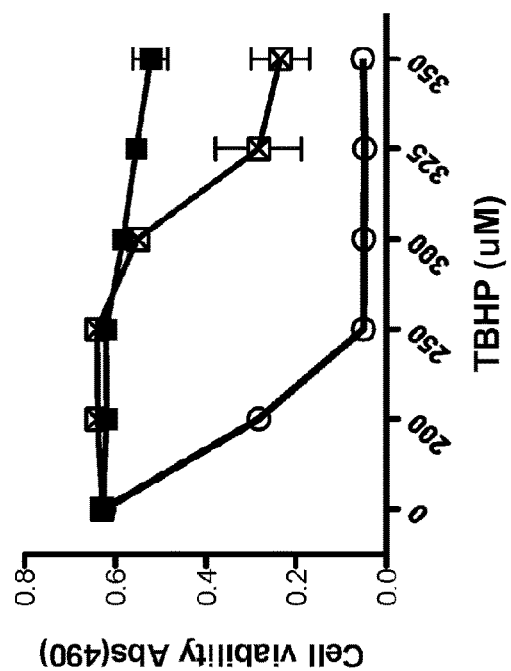
FIG. 6 shows the protective effect of Compound 9 on RPE cells through a preconditioning mechanism. RPE cells were incubated with: (A) ROS scavenger, tiron (disodium 4,5 dihydroxy-1,3 benzenedisulfonate) (1 mM); (B) PKC inhibitor (PKCI) chelerythrine (2 µM); or the (C) PKG inhibitor, Rp-Br-8-PET-cGMPS (500 µM) for 24 h in combination with Compound 9.
Figure 6A:
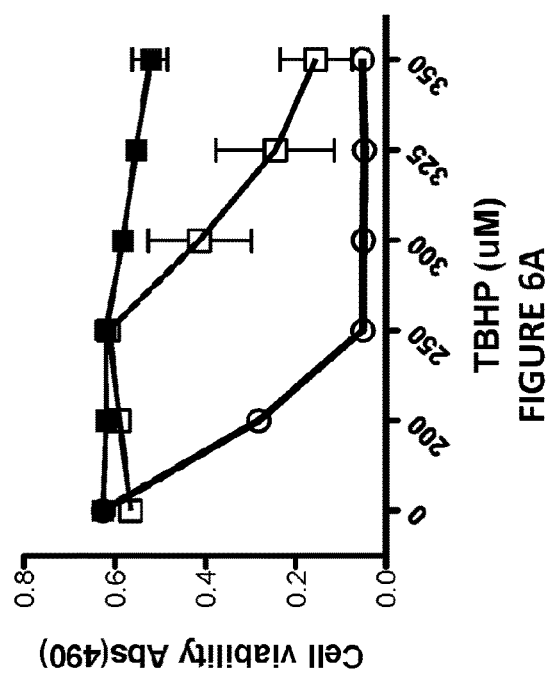
Figure 6B:
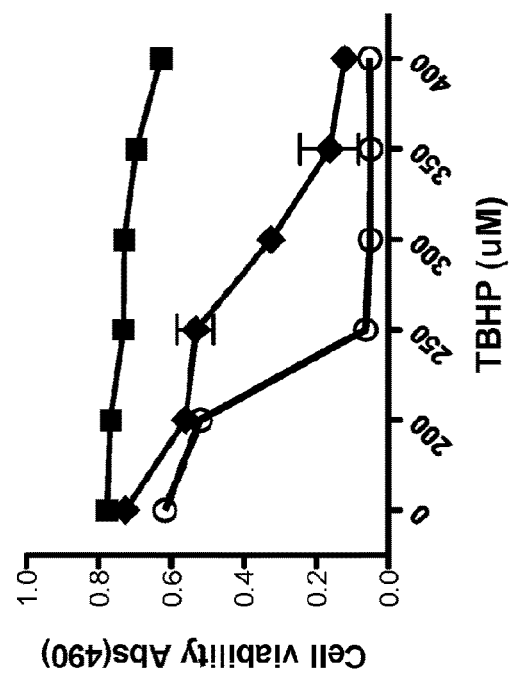

We used various metabolic inhibitors to obtain evidence that Compound 9 is functioning through a preconditioning mechanism. FIG. 6A shows that tiron, a scavenger of ROS, attenuates the protective effect caused by Compound 9, suggesting a role of ROS in the observed protection. FIG. 6B shows that chelerythrine, a broad inhibitor of protein kinase C (PKC), significantly reduces the protective effect of Compound 9. Finally, FIG. 6C shows that Rp-Br-8-PET-cGMPS, an inhibitor of PKG, reduces the protection by Compound 9, which is consistent with a role of PDE5 and PDE10 inhibition as shown in FIG. 5. Together, the results in FIG. 6 indicate that Compound 9 is very likely initiating a pharmacological preconditioning response.

Example 3

Intraperitoneal (I.P.) Administration of Compound 9 Provided Significant Protection Against Cell Death in a Rat Langendorff Model of Myocardial Ischemia The protective (preconditioning) effect of Compound 9 was evaluated in an art-recognized Langendorff model of ischemia/reperfusion injury. Compound 9 was administered via i.p. injection to test animals daily for two days, and animal hearts were then removed for performance of the Langendorff procedure (described above and known in the art).

Figure 7:
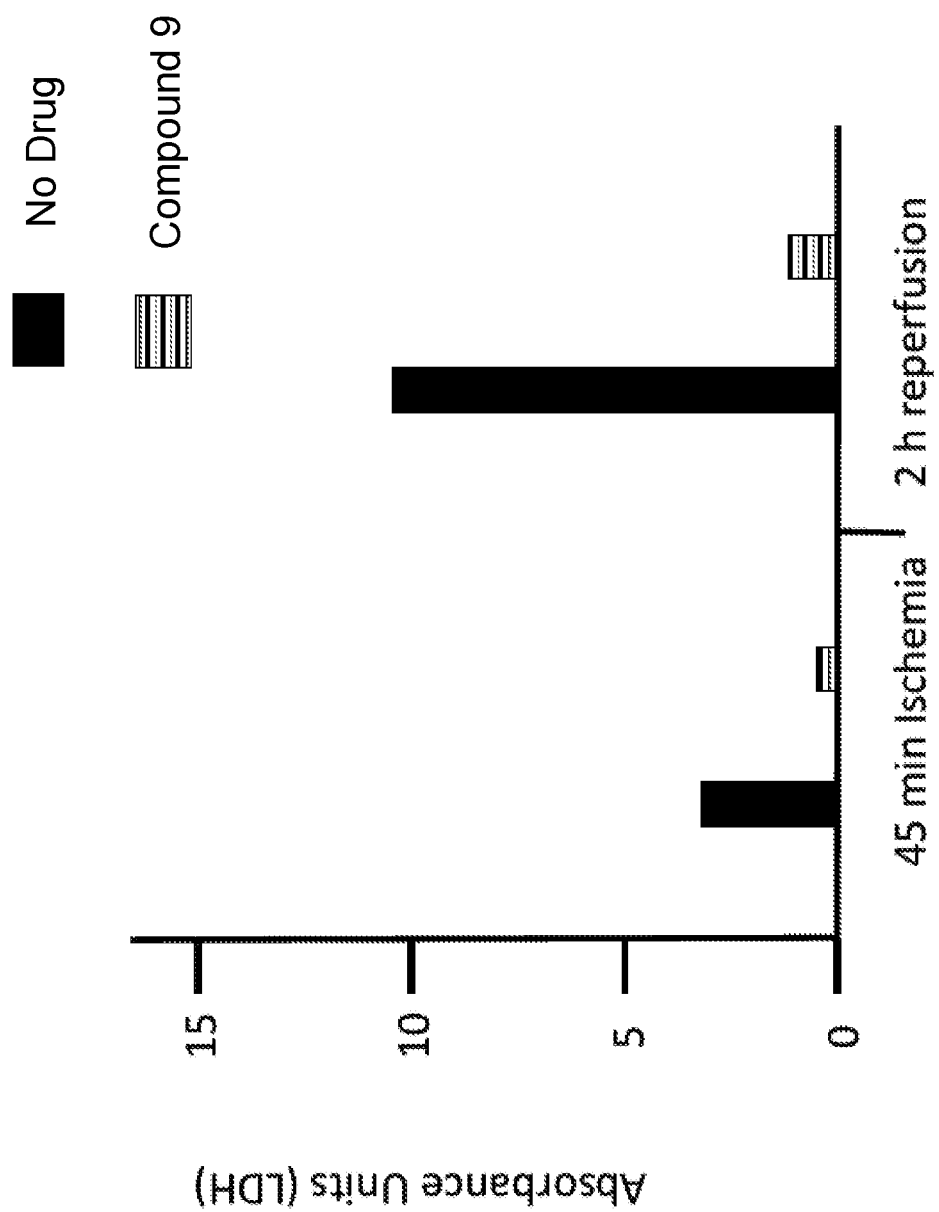
FIG. 7 demonstrates the protective effect of administering Compound 9 before performing the Langendorff procedure. Animals were administered either no drug or Compound 9 (0.7 mg/kg daily for 48 h) before isolation of the heart for analysis on the Langendorff apparatus. Total LDH levels (increased LDH levels indicating decreased cardiac cell viability) are shown after 45 min ischemia and 2 h of reperfusion, respectively (n=1 animal administered Compound 9, as compared to four control (no compound) animals).

As shown in FIG. 7, after 48 h of Compound 9 treatment prior to ischemia/reperfusion injury, levels of LDH released (LDH being a marker of diminished cell viability) were significantly lower after a 45 min period of no flow ischemia in the hearts from Compound 9-administered rats compared to the hearts from animals receiving the no drug administration (FIG. 7, 45 min ischemia results). The extent of protective effect observed for Compound 9 became more demonstrable during the 2 h reperfusion: Compound 9 markedly protected the heart against oxidative damage as seen by the decrease in LDH levels compared to the no drug control (compare 2 h reperfusion results of FIG. 7).

Figure 8A:
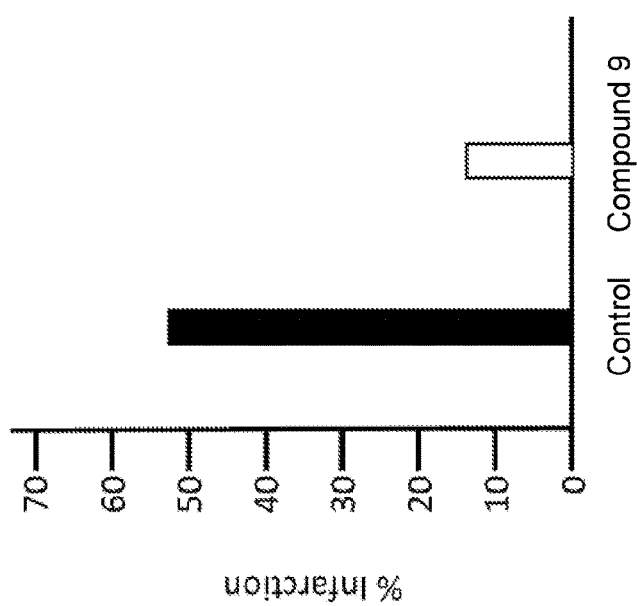
FIGS. 8A and 8B demonstrate infarct sizes of hearts as measured by triphenyltetrazolium chloride (TTC) staining.
Figure 8B:
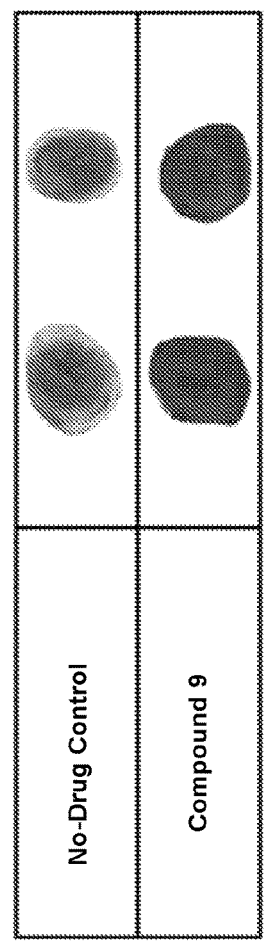

Infarct size was also significantly reduced in Compound 9-treated animals, as compared to control animals. As shown in FIGS. 8A and 8B, TTC staining (in which healthy tissue stains pink/red, whereas damaged tissue appears white) revealed that Compound 9-treated rats exhibited infarction sizes below 20%, as contrasted with animals administered no drug, which exhibited infarction sizes exceeding 50%.

Figure 9:
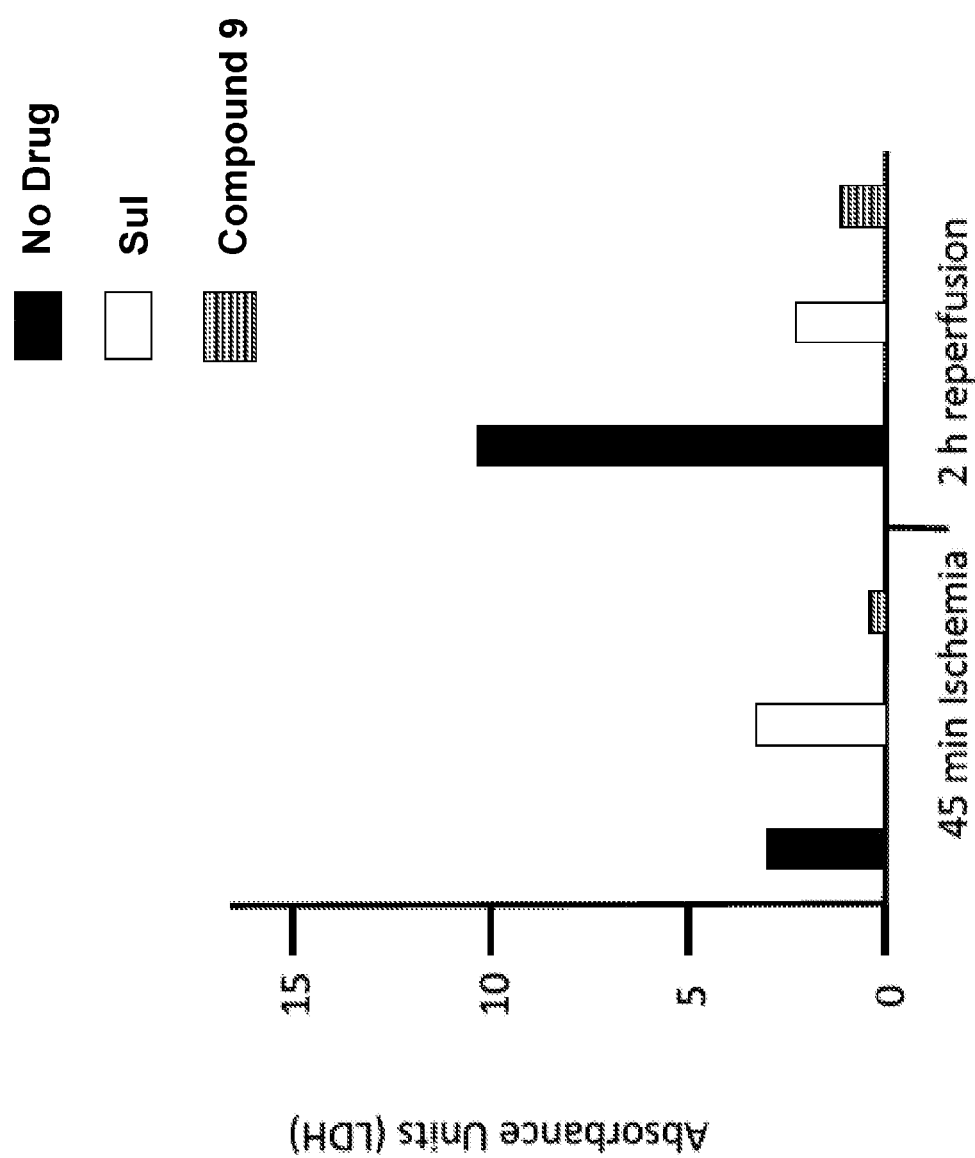
FIG. 9 shows that Compound 9 administered via i.p. injection at 0.7 mg/kg demonstrated a robust protective effect both during the 45 min ischemia phase of the Langendorff procedure and during the 2 h reperfusion phase. Sulindac exhibited no protective effect during the 45 min ischemia phase when administered at 0.7 mg/kg i.p. daily for 48 h prior to the Langendorff procedure, and the protective effect that was observed for sulindac during the 2 h reperfusion phase was not as robust as that observed for Compound 9.

Notably, Compound 9 exhibited enhanced potency of protective effect as compared to the protective effect previously described for sulindac. Specifically, as shown in FIG. 9, Compound 9 administered via i.p. injection at 0.7 mg/kg demonstrated robust protective effect both during the 45 min ischemia phase of the Langendorff procedure and during the 2 h reperfusion phase. Meanwhile, sulindac exhibited no protective effect during the 45 min ischemia phase when administered at 0.7 mg/kg i.p. daily for 48 h prior to the Langendorff procedure, in contrast to previous results in which a protective effect of sulindac was observed even during the 45 min ischemia phase, and the protective effect that was observed for sulindac during the 2 h reperfusion phase was not as robust as that observed for Compound 9, when both sulindac and Compound 9 were administered at the same dose (0.7 mg/kg) and via the same route of administration (i.p. injection).

The above studies therefore demonstrated that Compound 9 protected rat intact hearts (Langendorff model) against oxidative damage resulting from ischemia/reperfusion. Administration of Compound 9 to rats in vivo followed by removal of the heart, wash-out of the drug and subsequent ischemia and reperfusion resulted in substantial protection against ischemia-induced cell death relative to untreated hearts.

IPC is believed to be an important cellular protective mechanism, especially for organs that have high rates of respiration, such as the heart, brain and retina. There are other agents that have been reported to protect cells against ischemia/reperfusion damage, including the PDE5 inhibitor, sildenafil (Viagra™), and PPAR agonists (20, 21), that may act like pharmacologically preconditioning agents. Based on our previous studies (9, 10), and unpublished cell culture results, sulindac had appeared to be the most effective preconditioning agent, although its ability to inhibit prostaglandin synthesis from suppressing cyclooxygenase posed a significant limitation. In rodent cardiac studies, sulindac was highly effective in reducing the infarct size resulting from ischemic/reperfusion damage at a dose that was less than 20% (on a mg per kg basis) of the amount when used in humans as an anti-inflammatory drug (9). However, a more active sulindac derivative, with less or no COX inhibitory activity, would be safer and more efficacious. Thus, compounds of the present invention, e.g., Compound 9, that may be at least 10 times more active than sulindac (on a molar basis) in protecting RPE cells and other types of cells from oxidative damage, and which exhibit no significant COX inhibitory activity, are herein identified as likely to offer surprising and unexpected health advantages for clinical use.

All publications cited in the specification, including patent publications and non-patent publications, are indicative of the level of skill of those skilled in the art to which this invention pertains. All these publications are herein incorporate by reference to the same extent as if each individual publication were specifically and individually indicated as being incorporated by reference.

CITATIONS OF PUBLICATIONS REFERENCED HEREIN

1. Brot N, Weissbach L, Werth J, & Weissbach H (1981) Enzymatic reduction of protein-bound methionine sulfoxide. *Proceedings of the National Academy of Sciences of the United States of America* 78(4):2155-2158.
2. Weissbach H, Resnick L, & Brot N (2005) Methionine sulfoxide reductases: history and cellular role in protecting against oxidative damage. *Biochimica et biophysica acta* 1703(2):203-212.
3. Levine R L, Mosoni L, Berlett B S, & Stadtman E R (1996) Methionine residues as endogenous antioxidants in proteins. *Proceedings of the National Academy of Sciences of the United States of America* 93(26): 15036-15040.
4. Ruan H, et al. (2002) High-quality life extension by the enzyme peptide methionine sulfoxide reductase. *Proceedings of the National Academy of Sciences of the United States of America* 99(5):2748-2753.
5. Minniti A N, et al. (2009) Methionine sulfoxide reductase A expression is regulated by the DAF-16/FOXO pathway in Caenorhabditis elegans. *Aging cell* 8(6):690-705.
6. Minnerly J Z J, Aldunate R, Weissbach H, Jia K. (2013) Methionine sulfoxide reductase A mediates dietary restriction-induced lifespan extension in Caenorhabditis elgans. *Aging Sci.* 1(110):doi.10.4172/2329-8847.1000110.
7. Brunell D, Sagher D, Kesaraju S, Brot N, & Weissbach H (2011) Studies on the metabolism and biological activity of the epimers of sulindac. *Drug metabolism and disposition: the biological fate of chemicals* 39(6):1014-1021.
8. Marchetti M, et al. (2009) Sulindac enhances the killing of cancer cells exposed to oxidative stress. *PloS one* 4(6):e5804.
9. Moench I, Prentice H, Rickaway Z, & Weissbach H (2009) Sulindac confers high level ischemic protection to the heart through late preconditioning mechanisms. *Proceedings of the National Academy of Sciences of the United States of America* 106(46): 19611-19616.
10. Sur A, et al. (2014) Pharmacological protection of retinal pigmented epithelial cells by sulindac involves PPAR-alpha. *Proceedings of the National Academy of Sciences of the United States of America* 111(47): 16754-16759.
11. Bolli R (2000) The late phase of preconditioning. *Circulation research* 87(11):972-983.
12. Das A, Salloum F N, Xi L, Rao Y J, & Kukreja R C (2009) ERK phosphorylation mediates sildenafil-induced myocardial protection against ischemia-reperfusion injury in mice. *American journal of physiology. Heart and circulatory physiology* 296(5):H1236-1243.
13. Ravingerova T, et al. (2011) The role of PPAR in myocardial response to ischemia in normal and diseased heart. *General physiology and biophysics* 30(4):329-341.
14. Ayyanathan K, Kesaraju S, Dawson-Scully K, & Weissbach H (2012) Combination of sulindac and dichloroacetate kills cancer cells via oxidative damage. *PloS one* 7(7):e39949.
15. Gurpinar E, Grizzle WE, & Piazza GA (2014) NSAIDs inhibit tumorigenesis, but how? *Clinical Cancer Research.* (5): 1104-1113.
16. Giardiello F M, et al. (1993) Treatment of colonic and rectal adenomas with sulindac in familial adenomatous polyposis. *The New England journal of medicine* 328(18): 1313-1316.

17. Piazza G A, et al. (1997) Sulindac sulfone inhibits azoxymethane-induced colon carcinogenesis in rats without reducing prostaglandin levels. *Cancer research* 57(14):2909-2915.
18. Whitt J D, et al. (2012) A novel sulindac derivative that potently suppresses colon tumor cell growth by inhibiting cGMP phosphodiesterase and beta-catenin transcriptional activity. *Cancer Prev Res (Phila)* 5 (6): 822-833.
19. Gurpinar E, et al. (2013) A novel sulindac derivative inhibits lung adenocarcinoma cell growth through suppression of Akt/mTOR signaling and induction of autophagy. *Molecular cancer therapeutics* 12(5):663-674.
20. Lee, et al. (2016) f3-catenin nuclear translocation in colorectal cancer cells is suppressed by PDE10A inhibition, cGMP elevation, and activation of PKG. *Oncotarget.* 7:5353-65.
21. Thompson W J, et al. (2000) Exisulind induction of apoptosis involves guanosine 3',5'-cyclic monophosphate phosphodiesterase inhibition, protein kinase G activation, and attenuated beta-catenin. *Cancer Research* 60(13): 3338-3342.
22. Ferrera R., et al. (2009) One Hour Reperfusion is Enough to Assess Function and Infarct Size With TTC Staining in Langendorff Rat Model. *Cardiovascular Drugs and Therapy* 23(4):327-331.
23. Skrzypiec-Spring M, et al. (2007) Isolated heart perfusion according to Langendorff-Still viable in the new millennium. *J Pharmacol Toxicol Methods* 55:113-126.
24. Yoshida T, et al. (2000) Targeted disruption of the mouse SODI gene makes the heart vulnerable to ischemic reperfusion injury. *Circ Res* 86:264-269.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A pharmaceutical composition comprising the compound (Z)-2-(5,6-dimethoxy-2-methyl-1-(3,4,5-trimethoxybenzylidene)-1H-inden-3-1)acetic acid, or a pharmaceutically acceptable salt thereof, and a pharmaceutically acceptable carrier, wherein the amount of the compound is effective to protect cells against oxidative damage, and wherein the composition is in a form suitable for oral, parenteral or topical administration.

2. A method for protecting cells in a subject from oxidative damage which entails administering to the subject an effective amount of a compound which is (Z)-2-(5,6-dimethoxy-2-methyl-1-(3,4,5-trimethoxybenzylidene)-1H-inden-3-yl)acetic acid or a pharmaceutically acceptable salt thereof.

3. A method of preventing or reducing the extent of tissue damage of an ischemic event in a subject at elevated risk of an ischemic event, comprising:
  a. identifying a subject at elevated risk of an ischemic event; and
  b. administering a therapeutically effective amount of the compound (Z)-2-(5,6-dimethoxy-2-methyl-1-(3,4,5-trimethoxyb enzyli dene)-1H-inden-3-yl)acetic acid, or a pharmaceutically acceptable salt or prodrug thereof to the subject, thereby preventing or reducing the extent of tissue damage of an ischemic event in a subject at elevated risk of an ischemic event.

4. The method of claim 3, wherein the subject possesses one or more risk factors for an ischemic event selected from the group consisting of high blood pressure, heart disease, high cholesterol levels, sleep apnea, previous occurrence of stroke, smoking, excessive alcohol consumption and excessive weight.

5. The method of claim 3, wherein the ischemic event is an ischemic event of a tissue selected from the group consisting of the heart, brain, kidneys and liver.

6. The method of claim 3, further comprising administering to the subject a therapeutically effective amount of a medicament selected from the group consisting of aspirin, a blood pressure medication, a type II diabetes medication and an mTOR inhibitor, optionally wherein the type II diabetes medication is metformin, optionally wherein (Z)-2-(5,6-dimethoxy-2-methyl-1-(3,4,5-trimethoxybenzylidene)-1H-inden-3-yl)acetic acid, or a pharmaceutically acceptable salt or prodrug thereof and the medicament selected from the group consisting of aspirin, a blood pressure medication, a type II diabetes medication and an mTOR inhibitor are co-administered to the subject.

7. A method of treating a subject with retinitis pigmentosa, comprising administering to said subject a therapeutically effective amount of the compound (Z)-2-(5, 6-dimethoxy-2-methyl-1-(3, 4, 5-trimethoxybenzylidene)-1H-inden-3-yl)acetic acid, or a pharmaceutically acceptable salt or prodrug thereof.

8. A method of inhibiting production of ROS in a cell, in vivo or in vitro, comprising contacting the cell with an effective amount of the compound (Z)-2-(5,6-dimethoxy-2-methyl-1-(3,4,5-trimethoxybenzylidene)-1H-inden-3-yl) acetic acid, or a pharmaceutically acceptable salt thereof.

9. Amend as follows:
  A method of protecting a normal cell against oxidative damage, in vivo or in vitro, comprising contacting the cell with an effective amount of the compound (Z)-2-(5,6-dimethoxy-2-methyl-1-(3,4,5-trimethoxybenzylidene)-1H-inden-3-yl)acetic acid, or a pharmaceutically acceptable salt thereof.

10. The pharmaceutical composition of claim 1, wherein The composition is in the form of a tablet, powder, granule, capsule, liquid, gel, syrup, slurry, solution or suspension.

11. The pharmaceutical composition of claim 1, which is in the form of a solid.

12. The pharmaceutical composition of claim 11, wherein the carrier comprises lactose, mannitol, corn starch or potato starch.

13. Amend as follows:
  The pharmaceutical composition of claim 11, wherein the solid composition comprises at least one of a binder, a disintegrant, and a lubricant.

14. Amend as follows:
  The pharmaceutical composition of claim 13, wherein the solid composition further comprises at least one of a diluent, a buffering agent, a moistening agent, a preservative, and a flavoring agent.

15. The pharmaceutical composition of claim 1, which is in the form of an eye drop or eye ointment.

16. The pharmaceutical composition of claim 15, further comprising at least one of a buffering agent, an isotonizing agent, an antiseptic, a pH adjustor, a thickener, a chelating agent and a solubilizing agent.

17. The pharmaceutical composition of claim 15, further comprising purified lanolin, white petrolatum, macrogol, plastibase or liquid paraffin.

18. The pharmaceutical composition of claim 1, which is in the form of a liquid or semi-liquid.

19. The pharmaceutical composition of claim 18, which is in the form of a liniment, lotion, cream, ointment, paste, or drop.

20. The pharmaceutical composition of claim 19, which is in the form of an eye lotion.

21. The pharmaceutical composition of claim 20, further comprising a sterile aqueous solution.

22. The pharmaceutical composition of claim 19, which is in the form of a lotion or liniment and further comprises at least one of an agent to hasten drying and to cool the skin, and a moisturizer.

23. The pharmaceutical composition of claim 1, which is in the form of a semi-solid.

24. The pharmaceutical composition of claim 23, further comprising at least one of a hydrocarbon, a mucilage, an oil of natural origin, wool fat, a fatty acid, a surface active agent, and a suspending agent.

25. The pharmaceutical composition of claim 1, which is in a form suitable for parenteral administration.

26. The pharmaceutical composition of claim 25, wherein the carrier is aqueous.

27. The pharmaceutical composition of claim 26, wherein the carrier is a physiologically compatible buffer.

28. The pharmaceutical composition of claim 25, which is in the form of a suspension and the carrier comprises a lipophilic vehicle.

\* \* \* \* \*